United States Patent
Holzer et al.

(10) Patent No.: US 8,961,586 B2
(45) Date of Patent: Feb. 24, 2015

(54) BIFURCATED STENT ASSEMBLIES

(75) Inventors: Asher Holzer, Haifa (IL); Eli Bar, Moshav Megadim (IL); Ofir Paz, Rishon-LeZion (IL)

(73) Assignee: InspireMD Ltd., Tel Aviv, IL (US)

( * ) Notice: Subject to any disclaimer, the term of this patent is extended or adjusted under 35 U.S.C. 154(b) by 177 days.

(21) Appl. No.: 11/797,168

(22) Filed: May 1, 2007

(65) Prior Publication Data
US 2007/0276468 A1 Nov. 29, 2007

Related U.S. Application Data

(63) Continuation-in-part of application No. PCT/IB2006/051874, filed on May 24, 2006, and a continuation-in-part of application No. 11/582,354, filed on Oct. 18, 2006, now Pat. No. 8,043,323.

(Continued)

(51) Int. Cl.
| | | |
|---|---|---|
| A61F 2/82 | (2013.01) | |
| A61F 2/954 | (2013.01) | |
| A61F 2/90 | (2013.01) | |
| A61F 2/856 | (2013.01) | |
| A61F 2/852 | (2013.01) | |
| A61F 2/958 | (2013.01) | |

(52) U.S. Cl.
CPC . *A61F 2/90* (2013.01); *A61F 2/856* (2013.01); *A61F 2/954* (2013.01); *A61F 2/958* (2013.01); *A61F 2002/821* (2013.01); *A61F 2002/826* (2013.01); *A61F 2250/006* (2013.01); *A61F 2/852* (2013.01)

USPC ........................................... 623/1.35; 623/1.11

(58) Field of Classification Search
CPC ............... A61F 2/07; A61F 2/89; A61F 2/90; A61F 2002/826; A61F 2/958; A61F 2002/828; A61F 2/954; A61F 2/856
USPC ...................... 623/1.11, 1.12, 1.13, 1.16, 1.35
See application file for complete search history.

(56) References Cited

U.S. PATENT DOCUMENTS

| | | |
|---|---|---|
| 4,164,045 A | 8/1979 | Bokros et al. |
| 4,300,244 A | 11/1981 | Bokros |
| 4,321,711 A | 3/1982 | Mano |

(Continued)

FOREIGN PATENT DOCUMENTS

| | | |
|---|---|---|
| CN | 1414840 A | 4/2003 |
| EP | 0839506 | 5/1998 |

(Continued)

OTHER PUBLICATIONS

Fayad et al. "Clinical Imaging of the High-Risk or Vulnerable Atherosclerotic Plaque", Circulation Research, 89: 305-316, 2001.

(Continued)

*Primary Examiner* — Brian Pellegrino
(74) *Attorney, Agent, or Firm* — Haynes and Boone, LLP

(57) ABSTRACT

Disclosed is a stent assembly for expanding in vivo vessels, the assembly comprising first and second radially expandable mesh stents, wherein the first stent is separated by a predetermined distance from the second stent and a stent jacket spans the predetermined distance such that a first end of the jacket is operatively associated with the first stent and a second end of the jacket is operatively associated with the second stent.

39 Claims, 14 Drawing Sheets

Related U.S. Application Data

(60) Provisional application No. 60/683,788, filed on May 24, 2005, provisional application No. 60/716,100, filed on Sep. 12, 2005, provisional application No. 60/742,460, filed on Dec. 5, 2005, provisional application No. 60/852,392, filed on Oct. 18, 2006, provisional application No. 60/860,485, filed on Nov. 22, 2006, provisional application No. 60/860,486, filed on Nov. 22, 2006, provisional application No. 60/877,162, filed on Dec. 27, 2006.

(56) References Cited

U.S. PATENT DOCUMENTS

| | | | |
|---|---|---|---|
| 4,425,908 | A | 1/1984 | Simon |
| 4,723,549 | A | 2/1988 | Wholey et al. |
| 4,832,688 | A | 5/1989 | Sagae et al. |
| 4,865,017 | A | 9/1989 | Shinozuka |
| 4,873,978 | A | 10/1989 | Ginsburg |
| 4,969,891 | A | 11/1990 | Gewertz |
| 4,990,156 | A | 2/1991 | Lefebvre |
| 4,998,539 | A | 3/1991 | Delsanti |
| 5,019,090 | A | 5/1991 | Pinchuk |
| 5,122,154 | A | 6/1992 | Rhodes |
| 5,152,777 | A | 10/1992 | Goldberg et al. |
| 5,171,233 | A | 12/1992 | Amplatz et al. |
| 5,192,286 | A | 3/1993 | Phan et al. |
| 5,236,447 | A | 8/1993 | Kubo et al. |
| 5,330,482 | A | 7/1994 | Gibbs et al. |
| 5,366,504 | A | 11/1994 | Andersen et al. |
| 5,382,261 | A | 1/1995 | Palmaz |
| 5,383,887 | A | 1/1995 | Nadal |
| 5,403,341 | A | 4/1995 | Solar |
| 5,421,955 | A | 6/1995 | Lau et al. |
| 5,470,313 | A | 11/1995 | Crocker et al. |
| 5,486,183 | A | 1/1996 | Middleman et al. |
| 5,569,295 | A | 10/1996 | Lam |
| 5,591,228 | A | 1/1997 | Edoga |
| 5,713,948 | A | 2/1998 | Uflacker |
| 5,769,884 | A | 6/1998 | Solovay |
| 5,824,037 | A | 10/1998 | Fogarty et al. |
| 5,827,324 | A | 10/1998 | Cassell et al. |
| 5,833,651 | A | 11/1998 | Donovan et al. |
| 5,843,116 | A | 12/1998 | Crocker et al. |
| 5,843,161 | A | 12/1998 | Solovay |
| 5,871,538 | A | 2/1999 | Dereume |
| 5,908,448 | A | 6/1999 | Roberts et al. |
| 5,919,225 | A | 7/1999 | Lau et al. |
| 5,941,896 | A | 8/1999 | Kerr |
| 5,984,955 | A | 11/1999 | Wisselink |
| 6,007,543 | A | 12/1999 | Ellis et al. |
| 6,015,430 | A | 1/2000 | Wall |
| 6,015,432 | A | 1/2000 | Rakos et al. |
| 6,027,517 | A | 2/2000 | Crocker et al. |
| 6,030,414 | A | 2/2000 | Taheri |
| 6,042,597 | A | 3/2000 | Kveen et al. |
| 6,066,167 | A | 5/2000 | Lau et al. |
| 6,077,273 | A | 6/2000 | Euteneuer et al. |
| 6,096,027 | A | 8/2000 | Layne |
| 6,123,723 | A * | 9/2000 | Konya et al. .......... 623/1.11 |
| 6,152,144 | A | 11/2000 | Lesh et al. |
| 6,176,875 | B1 | 1/2001 | Lenker et al. |
| 6,245,089 | B1 | 6/2001 | Daniel et al. |
| 6,254,627 | B1 | 7/2001 | Freidberg |
| 6,263,880 | B1 | 7/2001 | Parker et al. |
| 6,306,162 | B1 | 10/2001 | Patel |
| 6,340,364 | B2 | 1/2002 | Kanesaka |
| 6,348,065 | B1 | 2/2002 | Brown et al. |
| 6,357,104 | B1 | 3/2002 | Myers |
| 6,361,558 | B1 | 3/2002 | Hieshima et al. |
| 6,369,039 | B1 | 4/2002 | Palasis et al. |
| 6,371,962 | B1 | 4/2002 | Ellis et al. |
| 6,383,171 | B1 | 5/2002 | Gifford et al. |
| 6,432,129 | B2 | 8/2002 | DiCaprio |
| 6,436,132 | B1 | 8/2002 | Patel et al. |
| 6,447,796 | B1 | 9/2002 | Vook et al. |
| 6,451,051 | B2 | 9/2002 | Drasler et al. |
| 6,461,381 | B2 | 10/2002 | Israel et al. |
| 6,464,722 | B2 | 10/2002 | Israel et al. |
| 6,468,230 | B2 | 10/2002 | Muni et al. |
| 6,488,703 | B1 | 12/2002 | Kveen et al. |
| 6,506,203 | B1 | 1/2003 | Boyle et al. |
| 6,540,773 | B2 | 4/2003 | Dong |
| 6,554,855 | B1 | 4/2003 | Dong |
| 6,602,285 | B1 | 8/2003 | Von Oepen et al. |
| 6,641,607 | B1 | 11/2003 | Hossainy et al. |
| 6,645,239 | B1 | 11/2003 | Park et al. |
| 6,669,717 | B2 | 12/2003 | Marotta et al. |
| 6,669,961 | B2 | 12/2003 | Kim et al. |
| 6,673,814 | B2 | 1/2004 | Joshi et al. |
| 6,676,695 | B2 | 1/2004 | Solem |
| 6,682,554 | B2 | 1/2004 | Oepen et al. |
| 6,702,849 | B1 | 3/2004 | Dutta et al. |
| 6,712,834 | B2 | 3/2004 | Yassour et al. |
| 6,712,842 | B1 | 3/2004 | Gifford, III et al. |
| 6,730,120 | B2 * | 5/2004 | Berg et al. .......... 623/1.42 |
| 6,755,856 | B2 | 6/2004 | Fierens et al. |
| 6,802,851 | B2 | 10/2004 | Jones et al. |
| 6,808,533 | B1 | 10/2004 | Goodwin et al. |
| 6,818,014 | B2 | 11/2004 | Brown et al. |
| 6,827,731 | B2 | 12/2004 | Armstrong et al. |
| 6,835,189 | B2 | 12/2004 | Musbach et al. |
| 6,893,457 | B2 | 5/2005 | Dong |
| 6,902,522 | B1 | 6/2005 | Walsh et al. |
| 6,918,920 | B1 | 7/2005 | Wang et al. |
| 6,919,100 | B2 | 7/2005 | Narayanan |
| 6,929,658 | B1 | 8/2005 | Freidberg et al. |
| 6,932,832 | B2 | 8/2005 | Patel et al. |
| 6,939,374 | B2 | 9/2005 | Banik et al. |
| 6,939,376 | B2 | 9/2005 | Shulze et al. |
| 6,953,476 | B1 | 10/2005 | Shalev |
| 6,981,986 | B1 | 1/2006 | Brown et al. |
| 6,997,946 | B2 | 2/2006 | Girton et al. |
| 7,011,676 | B2 | 3/2006 | Dong |
| 7,037,330 | B1 | 5/2006 | Rivelli, Jr. et al. |
| 7,041,129 | B2 | 5/2006 | Rourke et al. |
| 7,083,644 | B1 | 8/2006 | Moroni |
| 7,198,638 | B2 | 4/2007 | Dong |
| 7,491,225 | B2 | 2/2009 | Weber et al. |
| 7,722,634 | B2 | 5/2010 | Panetta et al. |
| 7,996,993 | B2 | 8/2011 | Gray et al. |
| 8,097,015 | B2 | 1/2012 | Devellian |
| 2002/0022860 | A1 | 2/2002 | Borillo et al. |
| 2002/0045917 | A1 | 4/2002 | Ambrisco et al. |
| 2002/0082685 | A1 | 6/2002 | Sirhan et al. |
| 2002/0111668 | A1 | 8/2002 | Smith |
| 2002/0128679 | A1 | 9/2002 | Turovskiy et al. |
| 2002/0161393 | A1 | 10/2002 | Demond et al. |
| 2003/0028239 | A1 | 2/2003 | Dong |
| 2003/0055452 | A1 | 3/2003 | Joergensen et al. |
| 2003/0093112 | A1 | 5/2003 | Addis |
| 2003/0100945 | A1 | 5/2003 | Yodfat et al. |
| 2003/0130718 | A1 | 7/2003 | Palmas et al. |
| 2003/0149464 | A1 | 8/2003 | Dong |
| 2003/0176884 | A1 | 9/2003 | Berrada et al. |
| 2003/0229389 | A1 | 12/2003 | Escano et al. |
| 2004/0030377 | A1 | 2/2004 | Dubson et al. |
| 2004/0054402 | A1 | 3/2004 | DiCarlo |
| 2004/0068314 | A1 | 4/2004 | Jones et al. |
| 2004/0111142 | A1 | 6/2004 | Rourke et al. |
| 2004/0116960 | A1 | 6/2004 | Demond et al. |
| 2004/0143272 | A1 | 7/2004 | Cully et al. |
| 2004/0158312 | A1 | 8/2004 | Chouinard et al. |
| 2004/0225322 | A1 | 11/2004 | Garrison et al. |
| 2004/0236407 | A1 | 11/2004 | Fierens et al. |
| 2004/0267347 | A1 | 12/2004 | Cervantes |
| 2004/0267352 | A1 | 12/2004 | Davidson et al. |
| 2005/0038503 | A1 | 2/2005 | Greenhalgh et al. |
| 2005/0049680 | A1 | 3/2005 | Fischell et al. |
| 2005/0110214 | A1 | 5/2005 | Shank et al. |
| 2005/0119688 | A1 | 6/2005 | Bergheim |
| 2005/0171591 | A1 | 8/2005 | McHale et al. |
| 2005/0182473 | A1 | 8/2005 | Eidenschink et al. |
| 2005/0187140 | A1 | 8/2005 | Hunter et al. |

(56) References Cited

U.S. PATENT DOCUMENTS

| | | |
|---|---|---|
| 2005/0222607 A1 | 10/2005 | Palmer et al. |
| 2005/0277976 A1 | 12/2005 | Galdonik et al. |
| 2006/0009835 A1 | 1/2006 | Osborne et al. |
| 2006/0085064 A1 | 4/2006 | Tuch |
| 2006/0116748 A1* | 6/2006 | Kaplan et al. ............... 623/1.11 |
| 2006/0155359 A1 | 7/2006 | Watson |
| 2006/0175727 A1 | 8/2006 | Fierens et al. |
| 2006/0259131 A1 | 11/2006 | Molaei et al. |
| 2006/0259137 A1 | 11/2006 | Artof et al. |
| 2007/0043428 A1 | 2/2007 | Jennings et al. |
| 2007/0135890 A1 | 6/2007 | Dong |
| 2007/0179593 A1 | 8/2007 | Fierens et al. |
| 2007/0179601 A1 | 8/2007 | Fierens et al. |
| 2007/0208374 A1 | 9/2007 | Boyle et al. |
| 2007/0213800 A1 | 9/2007 | Fierens et al. |
| 2007/0270902 A1 | 11/2007 | Slazas et al. |
| 2008/0023346 A1 | 1/2008 | Vonderwalde |
| 2008/0172082 A1 | 7/2008 | Holzer et al. |
| 2009/0012598 A1 | 1/2009 | Abbate et al. |
| 2009/0138070 A1 | 5/2009 | Holzer et al. |
| 2009/0248133 A1 | 10/2009 | Bloom et al. |
| 2010/0056907 A1 | 3/2010 | Rappaport et al. |
| 2010/0204772 A1 | 8/2010 | Holzer et al. |
| 2010/0222805 A1 | 9/2010 | Pal et al. |
| 2010/0241214 A1 | 9/2010 | Holzer et al. |
| 2011/0098739 A1 | 4/2011 | Bates |

FOREIGN PATENT DOCUMENTS

| | | |
|---|---|---|
| WO | 8809683 A1 | 12/1988 |
| WO | 9929262 A1 | 6/1999 |
| WO | 0130266 A1 | 5/2001 |
| WO | 03022325 A2 | 3/2003 |
| WO | WO 03/018079 | 3/2003 |
| WO | WO 2006/010130 | 1/2006 |
| WO | 2006116636 A1 | 11/2006 |
| WO | WO 2006/126182 | 11/2006 |
| WO | 2007067451 A2 | 6/2007 |
| WO | WO 2008/047367 | 4/2008 |
| WO | WO 2008/047368 | 4/2008 |
| WO | WO 2008/047369 | 4/2008 |
| WO | 2008062414 A2 | 5/2008 |

OTHER PUBLICATIONS

Chinese Patent Application # 200780046676.2 Office Action dated Apr. 28, 2011.
U.S. Appl. No. 12/445,972 Office Action dated Aug. 22, 2011.
Chinese Patent Application # 200780046659.9 Office Action dated May 11, 2011.
Chinese Patent Application # 200780046659.9 Office Action dated Oct. 26, 2011.
Haj et al., "Acquired Haemophilia A May be Associated with Clopidogrel", British Medical Journal, vol. 329, p. 323, Aug. 7, 2004.
Zakarija et al., "Clopidogrel-Associated TTP: An Update of Pharmacovigilance Efforts Conducted by Independent Researchers, Pharmaceutical Suppliers, and the Food and Drug Administration", Stroke—Journal of American Heart Association, vol. 35, pp. 533-537, Jan. 5, 2004.
Liistro et al., "Late Acute Thrombosis After Paclitaxel Eluting Stent Implantation", Heart Medical Journal, vol. 86, pp. 262-264, Sep. 2001.
Nguyen et al.,"Resistance to Clopidogrel: A Review of the Evidence", Journal of the American College of Cardiology, vol. 45, No. 8, pp. 1157-1164, Apr. 19, 2005.
U.S. Appl. No. 11/582,354 Official Action dated Jun. 14, 2010.
Holzer et al., U.S. Appl. No. 12/445,968 "Bifurcated stent assemblies," filed Apr. 17, 2009.
International Patent Application PCT/IL07/01442 Search Report dated Aug. 27, 2008.
International Patent Application PCT/IL07/01253 Search report dated Jun. 13, 2008.
International Patent Application PCT/IL07/01254 Search Report dated Sep. 30, 2008.
International Patent Application PCT/IL07/01255 Search Report dated Sep. 25, 2008.
U.S. Appl. No. 11/582,354 Official Action dated Nov. 4, 2010.
U.S. Appl. No. 12/445,968 Official Action dated Jan. 25, 2011.
U.S. Appl. No. 11/920,972 Official Action dated Nov. 30, 2011.
U.S. Appl. No. 11/920,972 Advisory Action dated Feb. 10, 2012.
U.S. Appl. No. 12/445,980 Official Action dated Dec. 5, 2011.
U.S. Appl. No. 11/920,972 Official Action dated Mar. 31, 2011.
Israel Patent Application # 198189 Official Action dated Jun. 1, 2011.
Israel Patent Application # 187516 Official Action dated Apr. 14, 2011.
Israel Patent Application # 198190 Official Action dated Jun. 1, 2011.
Israel Patent Application # 198665 Official Action dated Jun. 1, 2011.
U.S. Appl. No. 12/445,980 Official Action dated Apr. 28, 2011.
U.S. Appl. No. 12/445,968 Official Action dated Jun. 17, 2011.
Chinese Patent Application # 200780046697.4 Official Action dated Apr. 6, 2011.
U.S. Appl. No. 12/791,008 Office action dated Oct. 4, 2012.
U.S. Appl. No. 11/920,972 Office action dated Oct. 9, 2012.
IL Patent Application # 198,190 Office action dated Nov. 22, 2012.
European Patent Application # 07827415.6 Search report dated Feb. 13, 2013.
European Patent Application # 07827227.5 Search report dated Feb. 25, 2013.
U.S. Appl. No. 11/920,972 Office action dated Apr. 16, 2013.
European Patent Application # 07827228.3 Search report dated Mar. 8, 2013.
Israeli Patent Application # 198665 Office action dated Apr. 25, 2013.
International Application PCT/IB2011/055758 Search Report dated May 14, 2012.
U.S. Appl. No. 12/791,008 Official Action dated Mar. 26, 2012.
U.S. Appl. No. 12/445,972 Official Action dated Jun. 18, 2012.
U.S. Appl. No. 12/445,972 Official Action dated Mar. 26, 2012.
Israel Patent Application # 198188 Official Action dated Apr. 16, 2012.
Chinese Patent Application # 200780043259.2 Official Action dated Mar. 31, 2012.
Chinese Patent Application # 200780046697.4 Official Action dated Mar. 23, 2012.

* cited by examiner

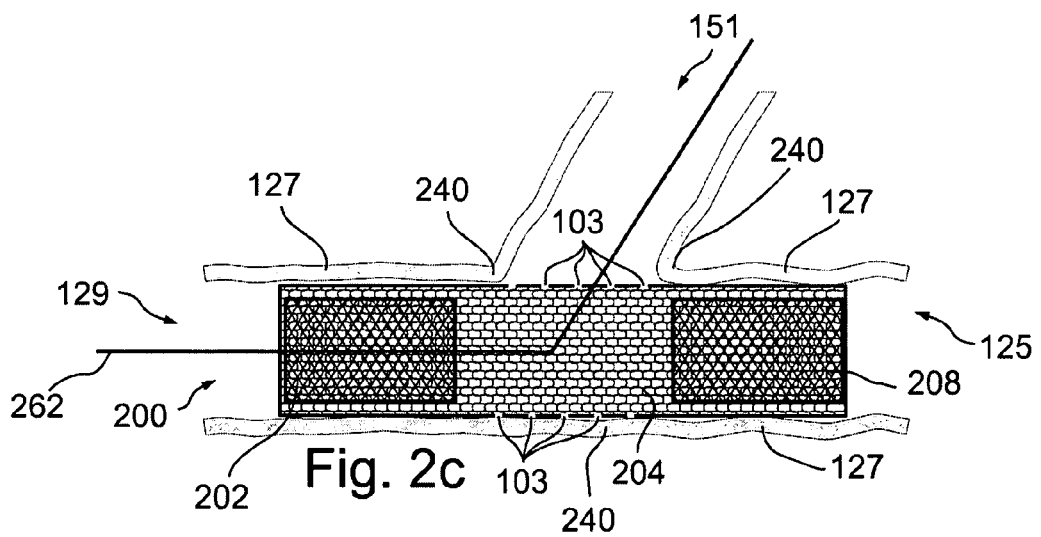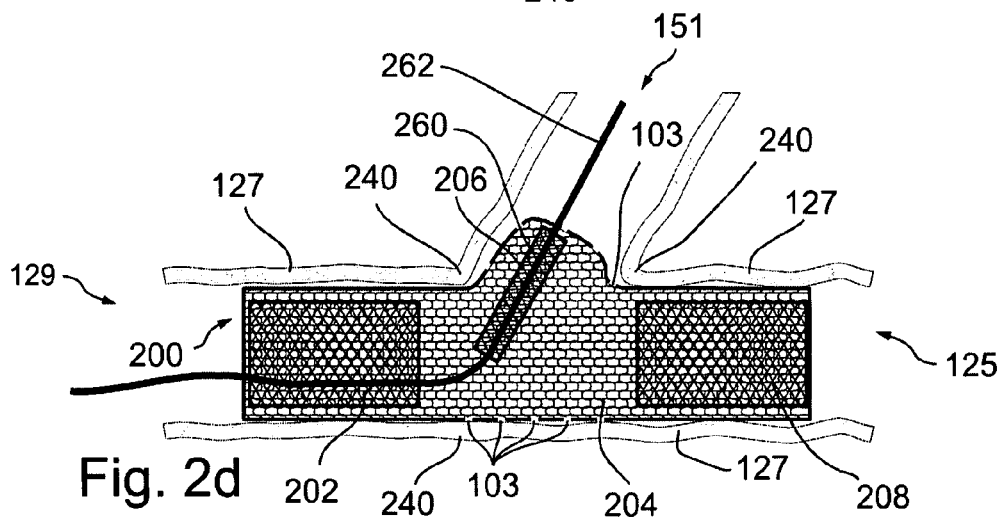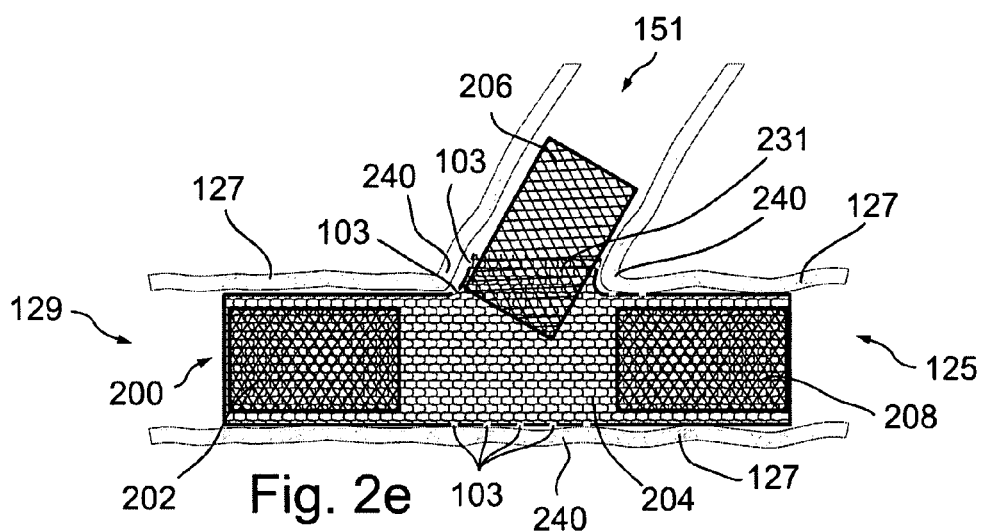

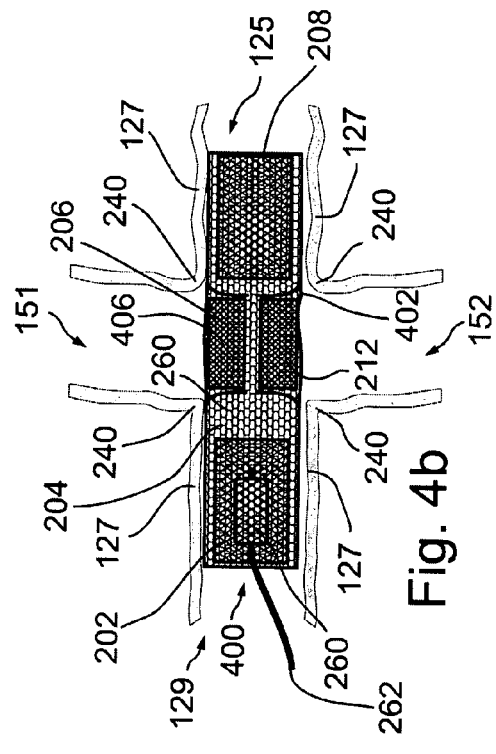
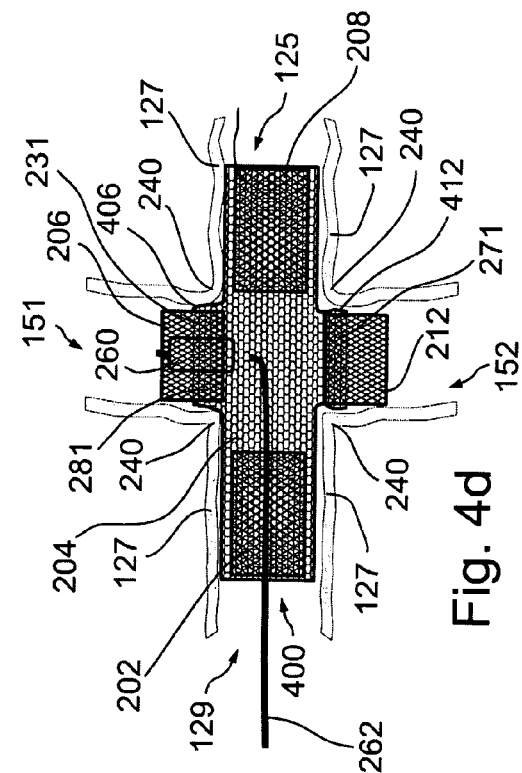
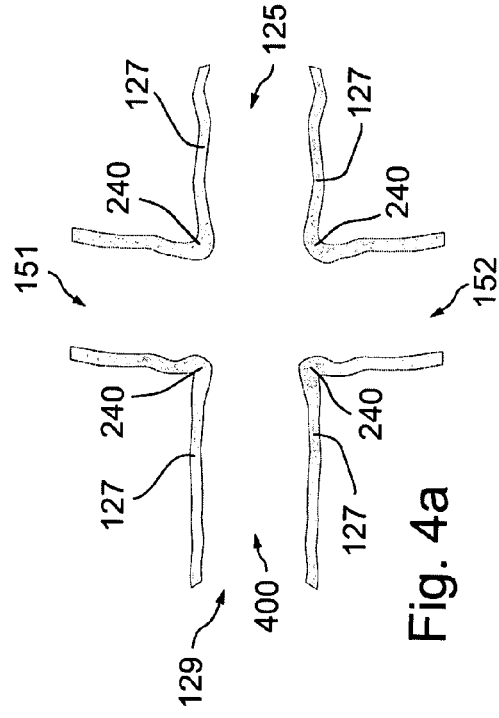
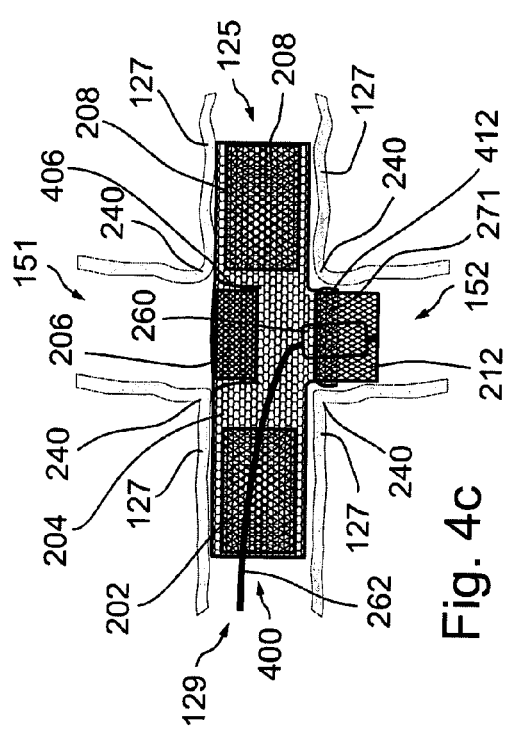

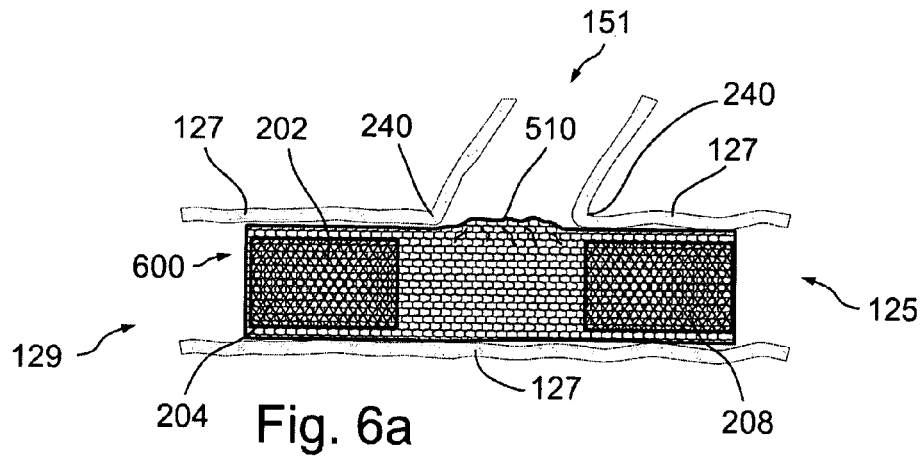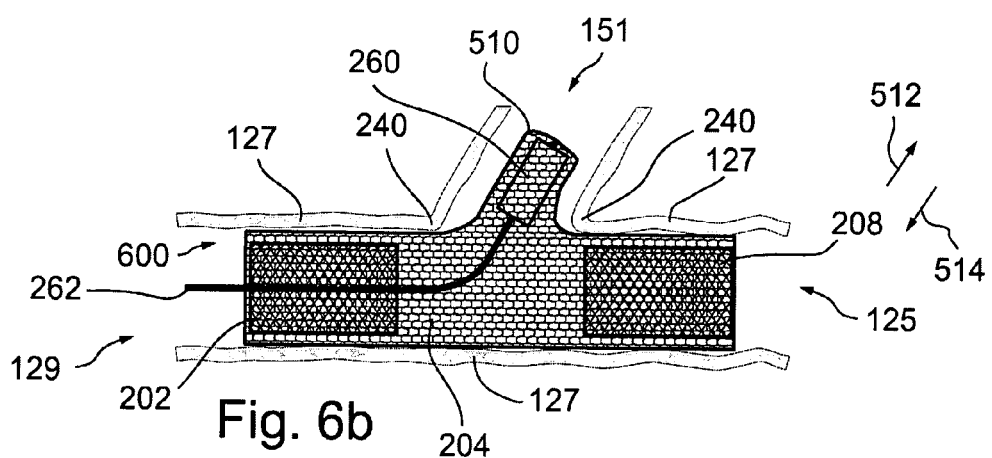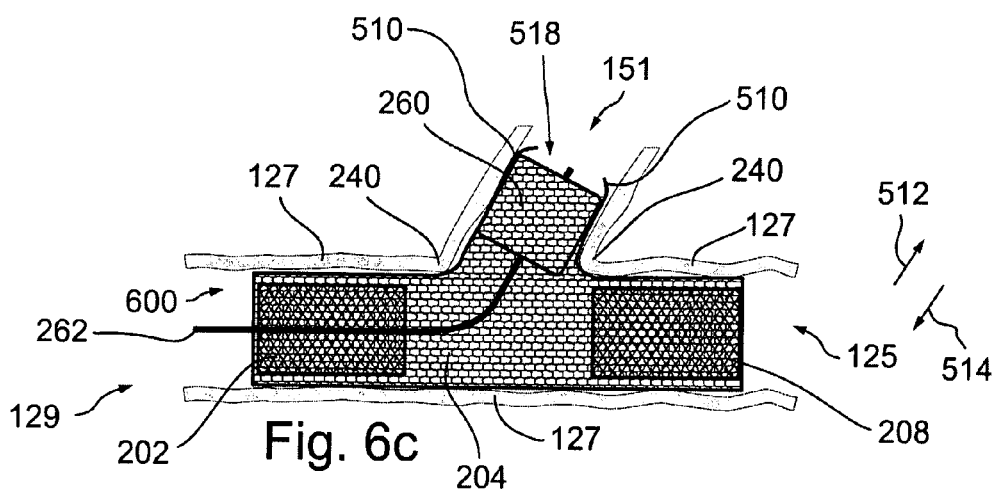

BIFURCATED STENT ASSEMBLIES

RELATIONSHIP TO EXISTING APPLICATIONS

This application is a continuation-in-part of PCT Patent Application No. PCT/IB2006/051874 filed May 24, 2006, which in turn claims the benefit of U.S. Provisional Patent Applications Nos. 60/683,788 filed May 24, 2005; 60/716,100 filed Sep. 12, 2005; and 60/742,460 filed Dec. 5, 2005.

This application is also a continuation-in-part of pending U.S. patent application Ser. No. 11/582,354 filed Oct. 18, 2006.

In addition, this application claims priority from U.S. Provisional Patent Applications Nos. 60/852,392 filed Oct. 18, 2006, 60/860,485 filed Nov. 22, 2006, 60/860,486 filed Nov. 22, 2006 and 60/877,162 filed Dec. 27, 2006.

The contents of the above Applications are hereby incorporated by reference as if fully disclosed herein.

FIELD AND BACKGROUND OF THE INVENTION

The present invention relates generally to stent assemblies that are deployed in bifurcated vessels.

While mono-tubular stents have resulted in improved long-term blood flow, stents are associated with severe problems when deployed in a bifurcated lumen, meaning a parent lumen from which a branch vessel splits. It is estimated that 15% to 20% of all stents are deployed at bifurcations.

Treatment of stenotic lesions at bifurcations is associated with increased early complications including compromise of either the branch vessel or the parent vessel and increased potential for restenosis.

One method for stenting a bifurcating vessel includes placing a first stent having a substantially circular side opening in a parent vessel and a second stent having a flared end for stenting the branch vessel.

The first stent is positioned in the lumen of the parent vessel and expanded, after which the second, flared stent is pressed through the side opening of the first stent and expanded in the branch vessel.

One drawback of this method is the difficulty of properly aligning the side opening of the first stent with the branch vessel bifurcation so that the branch vessel stent passes into the branch vessel. Another drawback of this system is that the second, flared, stent is difficult to position properly, and may protrude into the blood stream causing thrombosis.

Another method of treating bifurcations is called the crush method, an example of which is seen in U.S. Patent application 20050049680 (Fischell et al), the entirety of which is hereby incorporated by reference as if fully disclosed herein.

In this method, a first stent is placed into the branch vessel and expanded so that a portion of the stent protrudes into the parent vessel. A second stent is expanded in the parent vessel, crushing the protruding portion of the first stent against the parent vessel wall around the branch vessel opening.

If the first stent is not properly crushed, however, the end of the stent will protrude into the bloodstream, often resulting in thrombosis. Additionally, during crushing, the first stent may pull away from the branch vessel so that there is no support of the branch vessel where support is needed most. Finally, the crush method deposits a large amount of metal at the entrance to the branch vessel lumen, where the tissue is thin and often incapable of supporting the metallic bulk, resulting in restenosis.

SUMMARY OF THE INVENTION

In view of the drawbacks of the prior art stent systems for deployment in bifurcated vessels, it would be advantageous to have a bifurcation stent system that is easy to position, creates minimal resistance to flow, and maintains a minimal amount of metal bulk at the entrance to a branch vessel.

Some embodiments of the present invention successfully address at least some of the shortcomings of the prior art by providing a stent assembly comprising two radially expandable mesh stents separated by a distance with a common stent jacket spanning the distance therebetween.

In embodiments, the assembly is configured to be positioned so the mesh stents are located in a parent vessel on either side of a branch vessel bifurcation and the jacket spans the lumen associated with a bifurcation. A third contracted mesh stent is passed through an aperture in the jacket into the branch vessel and expanded. The aperture expands so that the third stent remains at least partially covered by the stent jacket and, in addition to the support provided by the stents, the stent jacket spanning between the first, second and third stents supports the stenotic tissue of the bifurcation therebetween.

In this manner, the bifurcation is opened without the bulk of more than one layer of metal as may be the case with bifurcation metal stents that are currently in use.

In further embodiments, portions of the stent, and/or stent jacket are coated and/or imbued with active pharmaceutical ingredients (APIs) for the purpose of preventing infection, inflammation, coagulation and/or thrombus formation.

Optionally, the two separated stents are covered by the jacket and mounted on a single angioplasty balloon and expand simultaneously within the vessel. Additionally, the two stents optionally positioned to stretch the jacket therebetween during expansion so that the jacket remains taut following removal of the balloon.

In embodiments in to order to easily form an opening in the stent jacket for passage of the third stent, the jacket is predilated with a balloon or multiple balloons via the "kissing" technique, or through direct dilation of the stents.

Additionally, the stents are optionally deployed using any one of several techniques, including inter alia pre dilatation angioplasty, post angioplasty, and the above noted "kissing technique" and direct dilation stenting techniques.

In other embodiments an end of the third stent, in an unexpanded state, is pressed into the jacket and the third stent is expanded, thereby stretching a portion of the stent jacket. Thereafter, the expanded jacket portion is punctured by a puncturing instrument, for example an expanding balloon, and the third stent is passed into the branch vessel and expanded.

In still other embodiments, a first mesh stent is placed in the parent vessel and the second mesh stent is placed in the branch vessel with a stent jacket passing therebetween. A third stent is passed through the jacket into the parent vessel, distal to the branch vessel, and expanded.

In still further embodiments, a stent assembly comprises two radially expandable mesh parent vessel stents separated by a distance with a common stent jacket spanning the distance therebetween; and includes one or more branch vessel stents that are transported, together with the parent vessel stents, to a bifurcation.

According to an aspect of the invention, there is provided a stent assembly for expanding in vivo vessels, the assembly comprising first and second radially expandable mesh stents, wherein the first stent is separated by a predetermined distance from the second stent and a stent jacket spans the predetermined distance such that a first end of the jacket is operatively associated with the first stent and a second end of the jacket is operatively associated with the second stent.

In embodiments, for example for use in a coronary vessel, the first stent is positioned between at least one millimeter and not more than about 20 millimeters from the second stent.

In other embodiments, the first stent is positioned about three millimeters from the second stent 208. Optionally, the first stent and second stent are placed in positions that stretch the jacket therebetween.

In embodiments, upon radial expansion of the first and second stents, the first jacket end expands radially and encircles at least a portion of the first stent and the second end of the jacket expands radially and encircles at least a portion of the second stent.

In embodiments, the stent jacket spanning the distance is configured to encircle an axially disposed third stent in a contracted state, the third stent being axially disposed and movably set on a guide wire while the first stent is contracted and the second stent is contracted.

In embodiments, the stent jacket spanning the distance is configured to encircle an axially disposed third stent in a contracted state while the assembly is being delivered to an in situ location.

In embodiments, the stent jacket spanning the distance is configured to encircle an axially disposed third stent in a contracted state following delivery of the first and second stents to an in situ location.

In embodiments, the stent jacket spanning the distance comprises at least one aperture configured to allow passage of the guide wire and the guide wire is configured to be manipulated through the aperture while the third stent is contracted.

In embodiments, the at least one aperture is additionally configured to encircle an outer surface of the third stent while the third stent is contracted.

In embodiments, the third stent is configured move along the guide wire through the aperture at an angle to an axis running between the first and second stent of at least about 15 degrees and no more than about 165 degrees.

In embodiments, the mean diameter of the at least one aperture is configured to expand when the contracted third stent is expanded while encircled by the aperture.

In embodiments, upon expansion of the third stent, at least a portion of the stent jacket spanning the distance is configured to encircle at least a portion of an outer surface of the third stent.

In embodiments, during expansion, the first stent and the second stent are of a sufficient diameter to press at least a portion of the inner walls of a parent vessel with a pressure of at least one atmosphere and no more than about 50 atmospheres.

In embodiments, during expansion, the first stent and the second stent are of a sufficient diameter to press at least a portion of the inner walls of a parent vessel with a pressure of about 15 atmospheres.

In embodiments, during expansion, the third stent is of a sufficient diameter to press at least a portion of the inner walls of a branch vessel with a pressure of at least one atmosphere and no more than about 50 atmospheres.

In embodiments, during expansion, the third stent is of a sufficient diameter to press at least a portion of the inner walls of a branch vessel with a pressure of about 15 atmospheres.

In embodiments, during expansion, the first stent and the third stent are of a sufficient diameter to press at least a portion of the inner walls of a parent vessel with a pressure of at least one atmosphere and no more than about 50 atmospheres.

In embodiments, during expansion, the first stent and the third stent are of a sufficient diameter to press at least a portion of the inner walls of a parent vessel with a pressure of about 15 atmospheres.

In embodiments, during expansion, the second stent is of a sufficient diameter to press at least a portion of the inner walls of a branch vessel with a pressure of at least one atmosphere and no more than about 50 atmospheres.

In embodiments, during expansion, the second stent is of a sufficient diameter to press at least a portion of the inner walls of a branch vessel with a pressure of about 15 atmospheres.

In embodiments, the third stent, while contracted, is configured to move along the guide wire and, following expansion of the first stent and the second stent, to have an end pressed into a portion of the stent jacket.

In embodiments, pressed portion of the stent jacket is configured to stretch when the third stent is expanded during the pressing.

In embodiments, the stretched portion of the stent jacket is configured to be punctured by a puncturing tool, wherein the resulting puncture is of a sufficient diameter to allow the third stent to pass through the puncture.

In embodiments, the third stent is configured to pass through the puncture at an angle to an axis running between the first and second stent of at least about 15 degrees and no more than about 165 degrees.

In embodiments, a portion of the stent jacket spanning the distance remains substantially intact following the puncturing.

In embodiments, portions of the intact portion form at least one fold as a result of at least one of:
  prior to the puncturing,
  during the puncturing, and
  following the puncturing.

In embodiments, at least a portion of the intact portion includes a pressure-sensitive self-adhering adhesive.

In embodiments, the adhesive is an adhesive from the group of adhesives comprising: fibrin, biological glue, collagen, hydrogel, hydrocolloid, collagen alginate, and methylcellulose.

In embodiments, at least a portion of the at least one fold is configured to adhere in response to pressure of at least about one atmosphere and no more than about 20 atmospheres.

In embodiments, the puncturing tool comprises an expandable balloon.

In embodiments, the stent jacket spanning the distance comprises at least one aperture configured to encircle the expandable balloon in a contracted state.

In embodiments, the at least one aperture is configured and to rip as the expandable balloon is inflated.

In embodiments, upon passage of the third stent through the puncture, at least a portion of the jacket is configured to encircle at least a portion of an outer surface of the third stent.

In embodiments, during expansion, the first stent and the second stent are of a sufficient diameter to press at least a portion of the inner walls of a parent vessel with a pressure of at least one atmosphere and no more than about 50 atmospheres.

In embodiments, during expansion, the first stent and the second stent are of a sufficient diameter to press at least a portion of the inner walls of a parent vessel with a pressure of about 15 atmospheres.

In embodiments, during expansion, the third stent is of a sufficient diameter to press at least a portion of the inner walls of a branch vessel with a pressure of at least one atmosphere and no more than about 50 atmospheres.

In embodiments, during expansion, the third stent is of a sufficient diameter to press at least a portion of the inner walls of a branch vessel with a pressure of about 15 atmospheres.

In embodiments, during expansion, the first stent and the third stent are of a sufficient diameter to press at least a portion of the inner walls of a parent vessel with a pressure of at least one atmosphere and no more than about 50 atmospheres.

In embodiments, during expansion, the first stent and the third stent are of a sufficient diameter to press at least a portion of the inner walls of a parent vessel with a pressure of about 15 atmospheres.

In embodiments, during expansion, the second stent is of a sufficient diameter to press at least a portion of the inner walls of a branch vessel with a pressure of at least one atmosphere and no more than about 50 atmospheres.

In embodiments, during expansion, the second stent is of a sufficient diameter to press at least a portion of the inner walls of a branch vessel with a pressure of about 15 atmospheres.

In embodiments, a first portion of the stent jacket spanning the distance is configured to encircle an axially disposed third stent in a contracted state while the assembly is being delivered to an in situ location.

In embodiments, the third stent is set at an angle to an axis passing through the first stent and the second stent of at least about 15 degrees and no more than about 165 degrees.

In embodiments, during expansion, the third stent is of a sufficient diameter to press at least a portion of the inner walls of a branch vessel with a pressure of at least one atmosphere and no more than about 50 atmospheres.

In embodiments, during expansion, the third stent is of a sufficient diameter to press at least a portion of the inner walls of a branch vessel with a pressure of about 15 atmospheres.

In embodiments, upon expansion, the third stent is configured to assume an angle to an axis passing through the first stent and the second stent of at least about 15 degrees and no more than about 165 degrees.

In embodiments, a second portion of the stent jacket spanning the distance is configured to additionally encircle an axially disposed fourth stent in a contracted state while the assembly is being delivered to an in situ location.

In embodiments, the fourth stent is set at an angle to an axis passing through the first stent and the second stent of at least about 15 degrees and no more than about 165 degrees.

In embodiments, the third stent is positioned to expand substantially outward and substantially radially opposite to the expansion of the fourth stent.

In embodiments, during expansion, the fourth stent is of a sufficient diameter to press at least a portion of the inner walls of a branch vessel with a pressure of at least one atmosphere and no more than about 50 atmospheres.

In embodiments, during expansion, the fourth stent is of a sufficient diameter to press at least a portion of the inner walls of a branch vessel with a pressure of about 15 atmospheres.

In embodiments, upon expansion, the fourth stent is configured to assume an angle to an axis passing through the first stent and the second stent of at least about 15 degrees and no more than about 165 degrees.

In embodiments, during expansion, the first stent and the second stent are of a sufficient diameter to press at least a portion of the inner walls of a parent vessel with a pressure of at least one atmosphere and no more than about 50 atmospheres.

In embodiments, during expansion, the first stent and the second stent are of a sufficient diameter to press at least a portion of the inner walls of a parent vessel with a pressure of about 15 atmospheres.

In embodiments, the stents comprise a metallic base from the group consisting of: stainless steel, nitinol, tantalum, MP35N alloy, a cobalt-based alloy, a cobalt-chromium alloy, platinum, titanium, or other biocompatible metal alloys.

In embodiments, the stents are selected from the group consisting of: a cardiovascular stent, a coronary stent, a peripheral stent, an abdominal aortic aneurysm stent, a cerebral stent, a carotid stent, an endovascular stent, an aortic valve stent, and a pulmonary valve stent.

In embodiments, the stent jacket comprises a material manufactured by a process from the group consisting of: interlacing knitting, interlocked knitting, braiding, interlacing, and/or dipping a porous mold into one or more reagents.

In embodiments, during expansion said stents are configured to expand in a manner that dilates the adjacent lumens.

In embodiments, following expansion the lumens are supported by one layer of stent metal.

According to an aspect of the present invention, there is provided a method for manufacturing a stent assembly for expanding in vivo vessel lumens, the method comprising: providing two axially aligned radially expandable mesh stents, comprising a first stent and a second stent, at a distance from each other, attaching a first end of a stent jacket to the first stent, and attaching a second end of the stent jacket to the second stent, such that an intermediate portion of the jacket spans the distance.

In embodiments, the method includes encircling a third stent in a contracted state coaxially aligned within the jacket.

In embodiments, the method includes axially setting the third stent within the jacket at an angle to an axis running between the first and second stent of at least about 15 degrees and no more than about 165 degrees.

In embodiments, the method includes encircling a fourth stent in a contracted state within the jacket.

In embodiments, the method includes axially setting the fourth stent within the jacket at an angle to an axis running between the first and second stent of at least about 15 degrees and no more than about 165 degrees.

In embodiments, the method includes positioning the third stent to expand substantially radially opposite to the expansion of the fourth stent.

In embodiments, the radially expandable stent comprises a metallic base from the group consisting of: stainless steel, nitinol, tantalum, MP35N alloy, a cobalt-based alloy, a cobalt-chromium alloy, platinum, titanium, or other biocompatible metal alloys.

In embodiments, the radially expandable stent comprises a bio degradable/bio-absorbable base from the group consisting of: PGLA, PLLA, PLA, bio-resorbable magnesium, or other bio resorbable compounds.

In embodiments, the jacket and the stents comprise a material selected from the group consisting of: polyethylene, polyvinyl chloride, polyurethane, nylon and a biocompatible polymer fiber.

In embodiments, the jacket and the stents comprise a material selected from the group consisting of: nitinol, stainless steel shape memory materials, metals, synthetic biostable polymer, a natural polymer, and an inorganic material. In embodiments, the biostable polymer comprises a material from the group consisting of: a polyolefin, a polyurethane, a fluorinated polyolefin, a chlorinated polyolefin, a polyamide, an acrylate polymer, an acrylamide polymer, a vinyl polymer, a polyacetal, a polycarbonate, a polyether, a polyester, an aromatic polyester, a polysulfone, and a silicone rubber.

In embodiments, the natural polymer comprises a material from the group consisting of: a polyolefin, a polyurethane, a Mylar, a silicone, and a fluorinated polyolefin.

In embodiments, the jacket and the stents comprise a material having a property selected from the group consisting of: compliant, flexible, plastic, and rigid.

In embodiments, the assembly includes an active pharmaceutical ingredient.

In embodiments, the API comprises a chemotherapeutic selected from the group consisting of peptides, proteins, nucleic acids, monoclonal antibodies, L-cell agonists, super oxide dismutase Interleukin-10, glucorticoids, sulphazalazine, calcitonin, insulin, 5-fluoracil, leucovorin, fluoropyrimidine S-1, 2'-deoxycytidine, analgesics, antibacterials, antibiotics, antidepressants, antihistamines, antihelminths, anti-inflammatory agents, antiirritants, antilipemics, antimicrobials, antimycotics, antioxidants, antipruritics, antiseptic, antiswelling agents, antiviral agents, antiyeast agents, astringents, topical cardiovascular agents, chemotherapeutic agents, corticosteroids, fungicides, hormones, hydroxyacids, lactams, non-steroidal anti-inflammatory agents, progestins, statines, sanatives and vasodilators and mixtures thereof.

In embodiments, the API comprises an analgesic selected from the group consisting of benzocaine, butamben picrate, dibucaine, dimethisoquin, dyclonine, lidocaine, pramoxine, tetracaine, salicylates and derivatives, esters, salts and mixtures thereof.

In embodiments, the API comprises an antibiotic selected from the group consisting of amanfadine hydrochloride, amanfadine sulfate, amikacin, amikacin sulfate, aminoglycosides, amoxicillin, ampicillin, ansamycins, bacitracin, beta-lactams, candicidin, capreomycin, carbenicillin, cephalexin, cephaloridine, cephalothin, cefazolin, cephapirin, cephradine, cephaloglycin, chloramphenicols, chlorhexidine, chlorhexidine gluconate, chlorhexidine hydrochloride, chloroxine, chlorquinaldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erythromycin stearate, farnesol, floxacillin, gentamicin, gentamicin sulfate, gramicidin, griseofulvin, haloprogin, haloquinol, hexachlorophene, iminocylcline, iodochlorhydroxyquin, kanamycin, kanamycin sulfate, lincomycin, lineomycin, lineomycin hydrochloride, macrolides, meclocycline, methacycline, methacycline hydrochloride, methenamine, methenamine hippurate, methenamine mandelate, methicillin, metronidazole, miconazole, miconazole hydrochloride, minocycline, minocycline hydrochloride, mupirocin, nafcillin, neomycin, neomycin sulfate, netilmicin, netilmicin sulfate, nitrofurazone, norfloxacin, nystatin, octopirox, oleandomycin, orcephalosporins, oxacillin, oxytetracycline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, spectinomycin, spiramycin, streptomycin, sulfonamide, tetracyclines, tetracycline, tobramycin, tobramycin sulfate, triclocarbon, triclosan, trimethoprim-sulfamethoxazole, tylosin, vancomycin, yrothricin and derivatives, esters, salts and mixtures thereof In embodiments, the API comprises an antihistamine selected from the group consisting of chlorcyclizine, diphenhydramine, mepyramine, methapyrilene, tripelennamine and derivatives, esters, salts and mixtures thereof.

In embodiments, the API comprises a corticosteroid selected from the group consisting of alclometasone dipropionate, amcinafel, amcinafide, amcinonide, beclomethasone, beclomethasone dipropionate, betamethsone, betamethasone benzoate, betamethasone dexamethasone-phosphate, dipropionate, betamethasone valerate, budesonide, chloroprednisone, chlorprednisone acetate, clescinolone, clobetasol, clobetasol propionate, clobetasol valerate, clobetasone, clobetasone butyrate, clocortelone, cortisone, cortodoxone, craposone butyrate, desonide, desoxymethasone, dexamethasone, desoxycorticosterone acetate, dichlorisone, diflorasone diacetate, diflucortolone valerate, diflurosone diacetate, diflurprednate, fluadrenolone, flucetonide, flucloronide, fluclorolone acetonide, flucortine butylesters, fludroxycortide, fludrocortisone, flumethasone, flumethasone pivalate, flumethasone pivalate, flunisolide, fluocinolone, fluocinolone acetonide, fluocinonide, fluocortin butyl, fluocortolone, fluorometholone, fluosinolone acetonide, fluperolone, fluprednidene acetate, fluprednisolone hydrocortamate, fluradrenolone, fluradrenolone acetonide, flurandrenolone, fluticasone, halcinonide, halobetasol, hydrocortisone, hydrocortisone acetate, hydrocortisone butyrate, hydrocortisone cyclopentylpropionate, hydrocortisone valerate, hydroxyltriamcinolone, medrysone, meprednisone, α-methyl dexamethasone, methylprednisolone, methylprednisolone acetate, mometasone furoate, paramethasone, prednisolone, prednisone, pregnenolone, progesterone, spironolactone, triamcinolone, triamcinolone acetonide and derivatives, esters, salts and mixtures thereof.

In embodiments, the API comprises a hormone selected from the group consisting of methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5a-dihydrotestosterone, testolactone, 17a-methyl-19-nortestosterone, desogestrel, dydrogesterone, ethynodiol diacetate, medroxyprogesterone, levonorgestrel, medroxyprogesterone acetate, hydroxyprogesterone caproate; norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogestrel, trimegestone, gestodene, nomegestrol acetate, progesterone, 5a-pregnan-3b,20a-diol sulfate, 5a-pregnan-3b,20b-diol sulfate, 5a-pregnan-3b.-ol-20-one, 16,5a-pregnen-3b-ol-20-one, 4-pregnen-20b-ol-3-one-20-sulfate, acetoxypregnenolone, anagestone acetate, cyproterone, dihydrogesterone, flurogestone acetate, gestadene, hydroxyprogesterone acetate, hydroxymethylprogesterone, hydroxymethyl progesterone acetate, 3-ketodesogestrel, megestrol, melengestrol acetate, norethisterone and derivatives, esters, salts and mixtures thereof.

In embodiments, the API comprises a non-steroidal anti-inflammatory agent selected from the group consisting of azelaic acid, oxicams, piroxicam, isoxicam, tenoxicam, sudoxicam, CP-14,304, salicylates, aspirin, disalcid, benorylate, trilisate, safapryn, solprin, diflunisal, fendosal, acetic acid derivatives, diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac, fenamates, mefenamic, meclofenamic, flufenamic, niflumic, tolfenamic acids, propionic acid derivatives, ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofen, pyrazoles, phenylbutazone, oxyphenbutazone, feprazone, azapropazone, trimethazone and derivatives, esters, salts and mixtures thereof.

In embodiments, the API comprises a vasodilator selected from the group consisting of ethyl nicotinate, capsicum extract and derivatives, esters, salts and mixtures thereof. In embodiments, the stent assembly includes a low-bulk mesh jacket designed to promote a stable layer of endothelial cells.

In embodiments, the mesh comprises fiber having a low diameter that allows each endothelial cell to fully cover and overlap each fiber, thereby forming a layer of endothelial cells that adhere to tissue on either side of the fiber. The thus formed endothelial layer is substantially stable with a substantially reduced tendency to break away and form emboli.

In embodiments, the mesh fiber comprises material that encourages adherence of endothelial cells, thereby encouraging endothelial layer stability.

In embodiments, each mesh fiber is spaced a distance from a neighboring fiber thereby preventing a single endothelial cell from adhering to more than one fiber, thereby reducing the chance that endothelial cells will break free of the stent, for example as a result of natural stent pulsation during blood flow.

In embodiments, the stent jacket optionally comprises a mesh that is knitted. In accordance with some embodiments of the present invention, the stent jacket mesh is optionally formed from a single fiber or a single group of fibers.

In embodiments, the stent assembly includes a stent jacket comprising an expansible mesh structure, formed of fibers of a diameter between about 7 micrometers and about 18 micrometers, the diameter having a property of forming a substantially stable layer of endothelial cells, covering the fibers, thus reducing platelet aggregation, and an expansible stent, operatively associated with the stent jacket.

In embodiments, the fiber diameter is between about 10 micrometers and bout 15 micrometers.

In embodiments, the fiber diameter is between about 11 micrometers and bout 14 micrometers.

In embodiments, the fiber diameter is between about 12 micrometers and bout 13 micrometers.

In embodiments, the fiber diameter is between about 12.5 micrometers. In embodiments, the mesh is formed as a single knit. In embodiments, the fiber is formed from multiple filaments.

In embodiments, the mesh jacket structure comprises a retracted state and a deployed state, and further in the deployed state, the mesh structure defines apertures having a minimum center dimension, which is greater than about 180 micrometers, thus minimizing occurrences of a single endothelial cell adhering to more than one fiber, across one of the apertures, and reducing a chance of endothelial cells breaking free as a result of natural stent pulsation with blood flow.

In embodiments, the minimum center dimension is greater than about 200 micrometers.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

BRIEF DESCRIPTION OF THE DRAWINGS

The invention of stent assemblies configured for assembling in bifurcating vessels is herein described, by way of example only, with reference to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-1d show deployment of prior art stents in bifurcating vessels;

FIGS. 2a-2e show stents and stent jackets being deployed in cross sections of bifurcating vessels, according to embodiments of the invention; and FIGS. 3a-8d show alternative embodiments of the stents and stent jackets of FIG. 2e being deployed in cross sections of bifurcating vessels, according to embodiments of the invention.

DESCRIPTION OF THE PREFERRED EMBODIMENTS

Figure 1A:
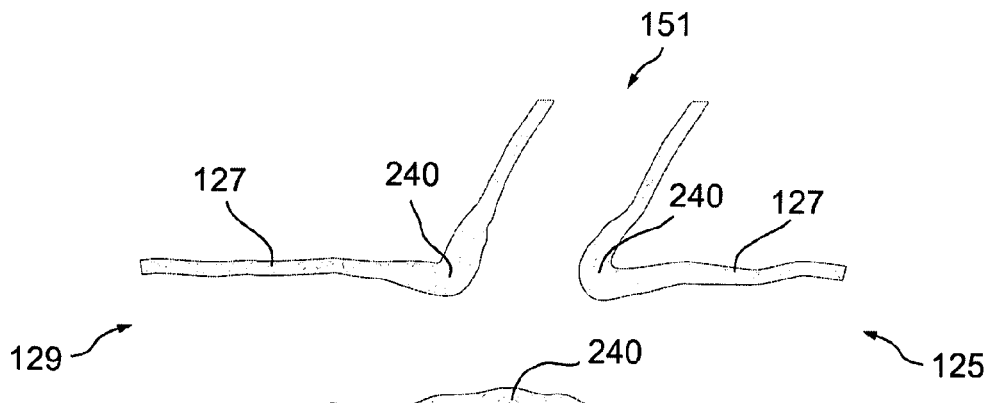

The present invention, which relates to stent assemblies configured for assembling in bifurcating vessels, is herein described, by way of example only, with reference to the accompanying drawings. The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings:

In FIG. 1a, arteries 127 form an upper branch vessel lumen 151, a proximal parent vessel lumen 129 and a distal parent vessel lumen 125.

Figure 1B:
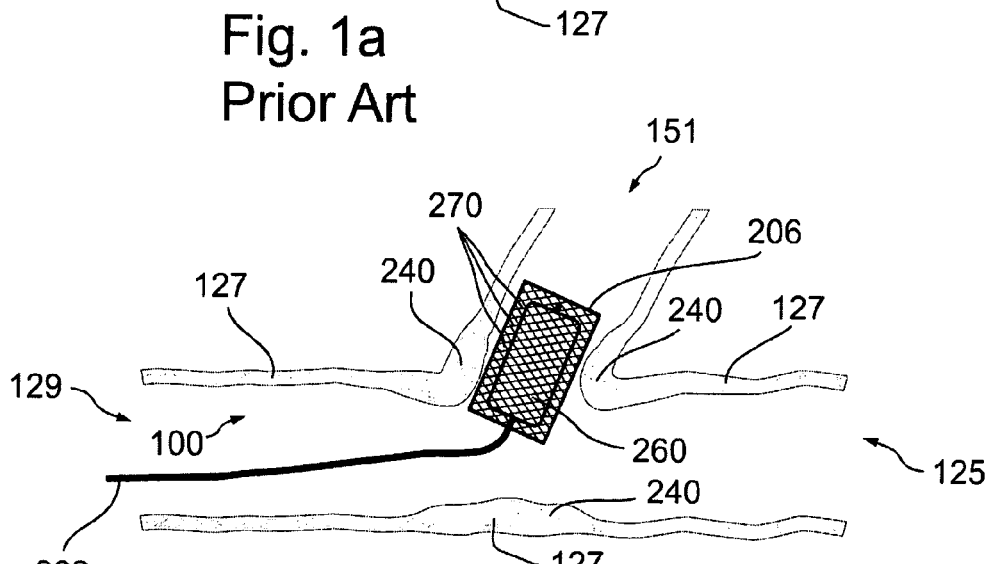
Figure 1C:
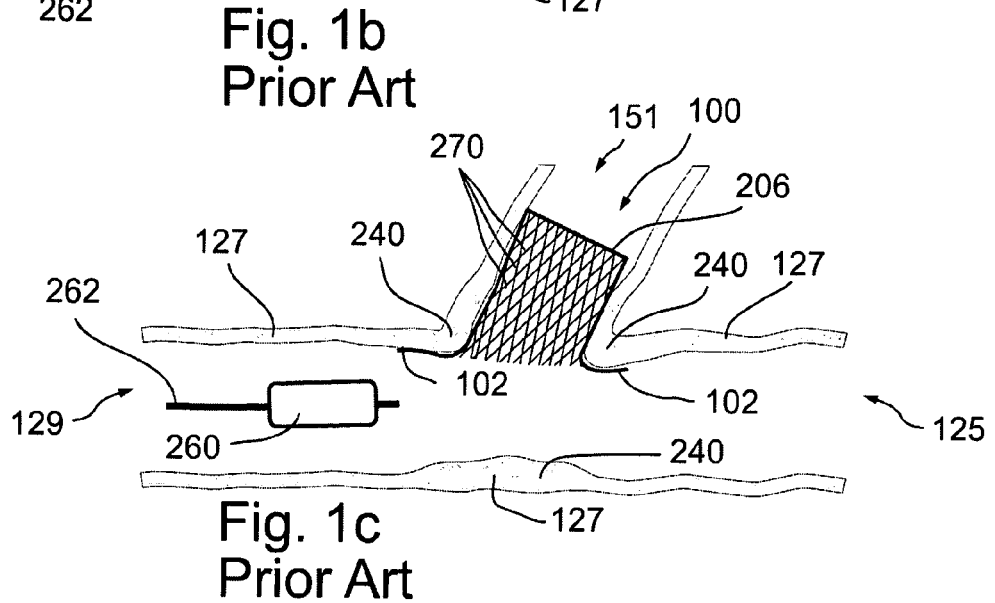
Figure 1D:
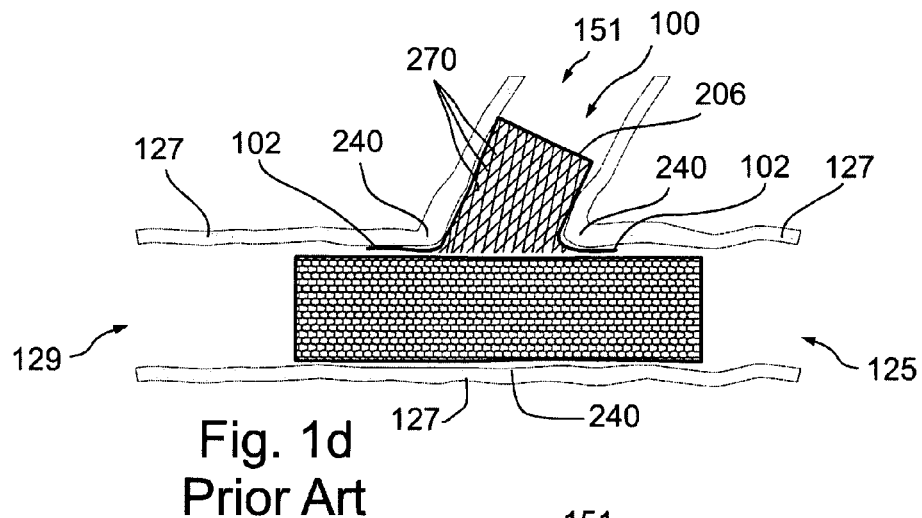

FIGS. 1b-1d show the crush method, noted above, for treating a bifurcation. As seen in FIG. 1b, a crush stent assembly 100 comprises a branch stent 206 configured for expansion in upper branch lumen 151. Branch stent 206, shown herein without a jacket, comprises a metal or polymer tubular structure having mesh-like, apertures 270. Branch stent 206 is shown encircling a balloon 260 and, upon expansion of balloon 260, branch stent 206 expands radially outward.

As seen in FIG. 1c, branch stent 206 has expanded radially in upper branch lumen 151 so that branch stent 206 presses against a stenotic area of tissue 240, thereby compressing and cracking stenotic area 240 radially outward within upper branch lumen 151. To further ensure flow of blood, a second balloon (not shown) is expanded against a flange 102 to crush flange 102 into proximal lumen 129 and into distal lumen 125.

Deployed stent assembly 100 crushes stenotic tissue 240 in lumens 151, 129 and 125, thereby allowing better circulation through arteries 127. However, as noted above and seen in FIG. 1d, branch stent 206 creates a significant amount of metal related to flange 102 that may subject artery walls 127 to restenosis, in addition to causing turbulence and thrombosis formation.

Figure 2A:
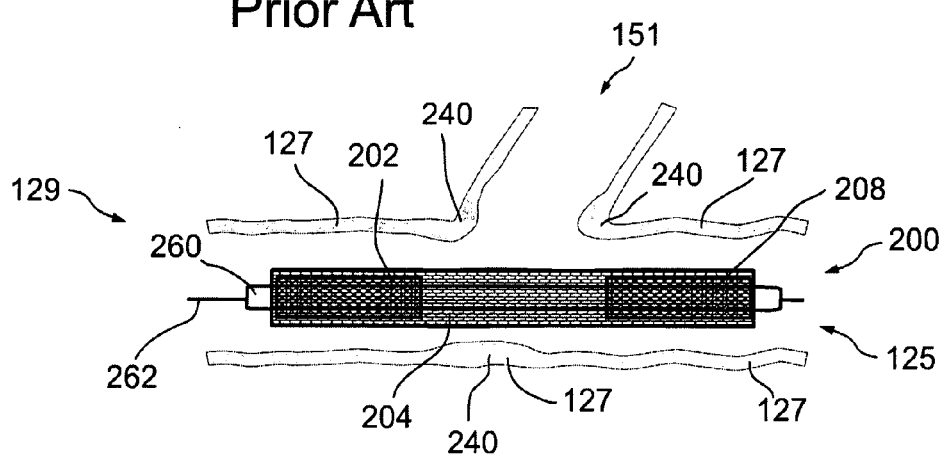

Referring to FIG. 2a, in an embodiment of the present invention, a stent system 200, comprises a proximal parent vessel stent 202 and a distal parent vessel stent 208 that are covered by an external jacket 204. Assembly 200 is positioned in artery 127 so that proximal stent 202 is positioned in proximal lumen 129 and distal stent 208 is positioned in distal lumen 125. In embodiments, for example for use in a coronary vessel, proximal stent 202 is positioned between at least one millimeter and not more than about 20 millimeters from distal stent 208. In other embodiments, proximal stent 202 is positioned about three millimeters from distal stent 208. Optionally, proximal stent 202 and distal stent 208 are placed in positions that stretches external jacket 204 therebetween.

In alternative embodiments proximal stent 202 and distal stent 208 are configured and appropriately sized as cardiovascular stents, peripheral stents, abdominal aortic aneurysm stents, cerebral stents, carotid stents, endovascular stents, aortic valve stents, and pulmonary valve stents.

Figure 2B:
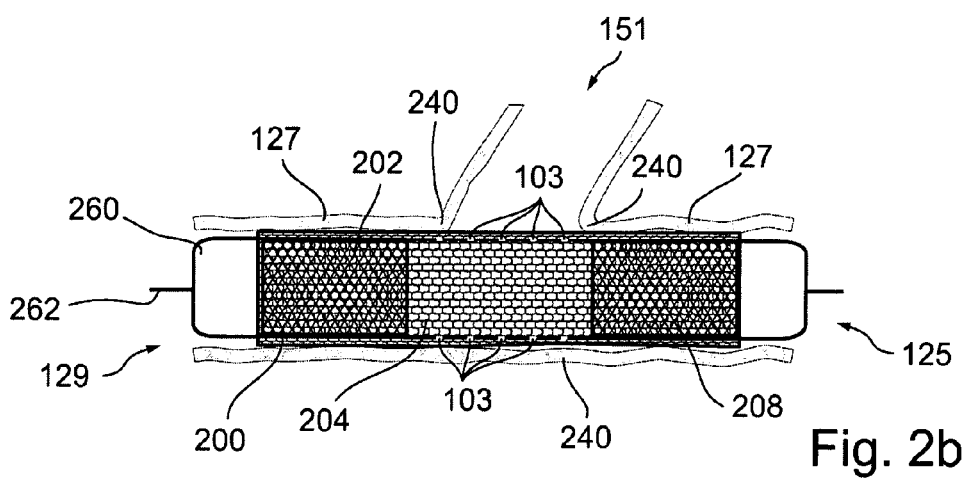

As seen in FIG. 2b, balloon 260 has been inflated, thereby expanding stents 202 and 208 so that stent jacket 204 spans upper branch lumen 151.

Optionally, balloon 260 is inflated in a manner that crushes stent jacket 204 to aid in opening in lumens 151, 129 and 125 and to avoid jailing of upper branch lumen 151 by stent jacket 204.

As seen in FIG. 2c, balloon 260 has been removed and the structure of stent jacket 204 can be appreciated. Stent jacket 204 typically comprises a knitted material having large apertures 103.

As seen in FIG. 2d, branch stent 206 positioned on balloon 260 has been pressed into stent jacket 204, through one of apertures 103. As seen in FIG. 2e, branch stent 206 has been expanded, thereby expanding aperture 103 and causing an encircling portion of jacket 231 to encircle branch stent 206.

In addition to the support provided by stents 202, 206 and 208, stent jacket 204 spanning therebetween, supports stenotic tissue 240 at the bifurcation of upper branch lumen 151. Using stent jacket 204 as a support along the bifurcation of upper branch lumen 151 results in low bifurcation-related bulk that could cause restenosis and/or thrombosis noted above.

In alternative embodiments, balloon 260 (FIG. 2d) is first used alone to predilate one of apertures 103, after which unexpanded branch stent 206 is pressed through predilated aperture 103 and expanded in upper branch lumen 151.

In embodiments, stents 202, 206 and 208 comprise any metallic base including, inter alia: stainless steel, nitinol, tantalum, MP35N alloy, a cobalt-based alloy, a cobalt-chromium alloy, platinum, titanium, or other biocompatible metal alloys.

In further embodiments, stents 202, 206 and 208 are deployed in any vessel comprising, inter alia: cardiovascular tissue, peripheral tissue, an abdominal aortic aneurysm, cerebral tissue, carotid tissue, endovascular tissue, aortic valves, and/or pulmonary tissue.

In still further embodiments, stent jacket 204 comprises any material manufactured by a process including, inter alia: interlacing knitting, interlocked knitting, braiding, interlacing, and/or dipping a porous mold into one or more reagents.

As used herein, any reference to a "knitted material" includes any material that is manufactured by a knitting process, including, inter alia: a material knitted from a single fiber, similar to the process used in pantyhose nylon; a double fiber knit, referred to as a "double knit material"; and includes fibers, either mono filament or multi filament fiber of, inter alia: polyethylene, polyvinyl chloride, polyurethane, nylon, a biocompatible polymer fiber, and stainless steal nitinol, or any other metal.

In embodiments, proximal stent 202, distal stent 208 and branch stent 206 comprise a metallic base from the group consisting of: stainless steel, nitinol, tantalum, MP35N alloy, a cobalt-based alloy, a cobalt-chromium alloy, platinum, titanium, or other biocompatible metal alloys.

In embodiments, proximal stent 202, distal stent 208 and branch stent 206 are manufactured with sufficient diameters to press at least a portion of the inner walls of artery 127 with a pressure of at least one atmosphere and no more than about 50 atmospheres. In embodiments, proximal stent 202, distal stent 208 and branch stent 206 are manufactured with sufficient diameters to press at least a portion of the inner walls of artery 127 with a pressure of about 15 atmospheres.

Figure 3A:
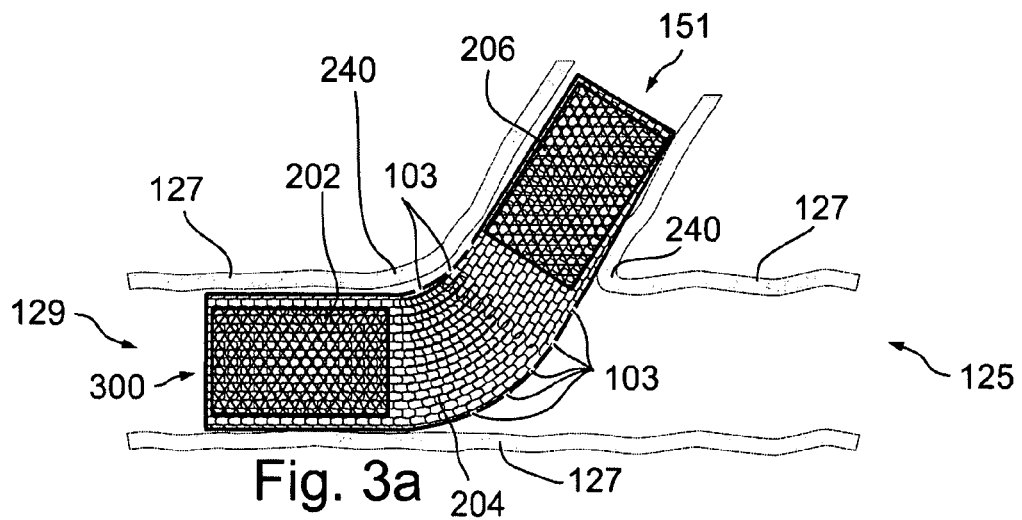

FIG. 3a shows a stent system 300 in which proximal stent 202 has been deployed in proximal lumen 129, and branch stent 206 has been deployed in upper branch lumen 151, while stent jacket 204 spans across distal lumen 125. Typically, upper branch lumen 151 has a smaller diameter than proximal lumen 129 and first balloon (not shown) having a smaller expanded diameter is used to expand branch stent 206.

Figure 3B:
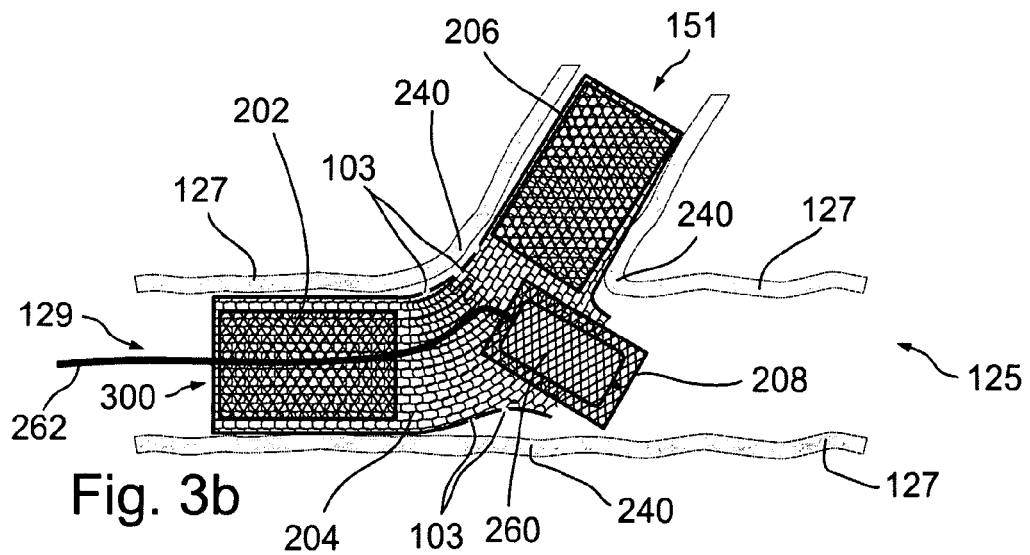

As seen in FIG. 3b, following expansion of stent 206, a second balloon 260 having a large expanded diameter is used to expand proximal lumen stent 202.

Figure 3C:
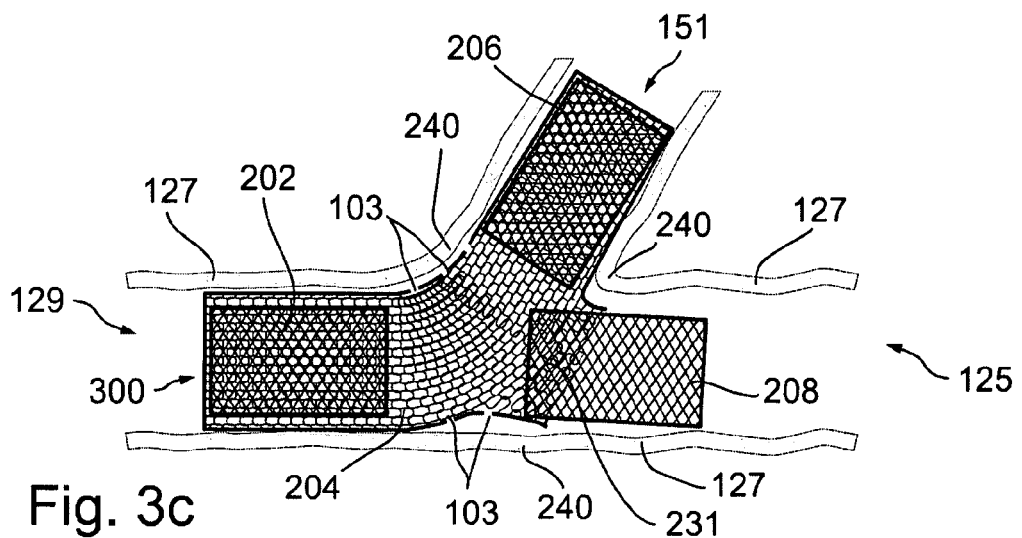

As seen in FIG. 3b, distal parent vessel stent 208 is pushed through apertures 103. As seen in FIG. 3c and distal parent vessel stent 208 has been expanded in distal lumen 125.

Referring to FIG. 4a, arteries 127 include a lower side branch lumen 152. As seen in FIG. 4b, a dual branch stent assembly 400 comprises stent jacket 204 having an upper sleeve 406 that is partially inside-out and surrounding upper branch stent 206. Stent jacket 204 further comprises a lower sleeve 412 that is inside out and surrounding a lower branch stent 212.

Dual branch stent assembly 400 has been positioned so that distal stent 208, upon expansion with a balloon (not shown), opens distal lumen 125. Proximal stent 202 is then expanded with balloon 260 to open proximal lumen 129.

As seen in FIG. 4c, balloon 260 has been positioned inside lower branch stent 212 and during expansion, balloon 260 is used to push lower branch stent 212 into lower branch lumen 152, thereby straightening lower jacket 204 so that sleeve 412 is no longer inside-out. Balloon 260 then expands lower branch stent 212 to open lower branch lumen 152.

As seen in FIG. 4d, balloon 260 has been positioned inside upper branch stent 206 and, during expansion, balloon 260 is used to push upper branch stent 206 into upper branch lumen 151, thereby straightening upper branch sleeve 406. Balloon 260 then expands upper branch stent 206 to open upper branch lumen 151.

Figure 4E:
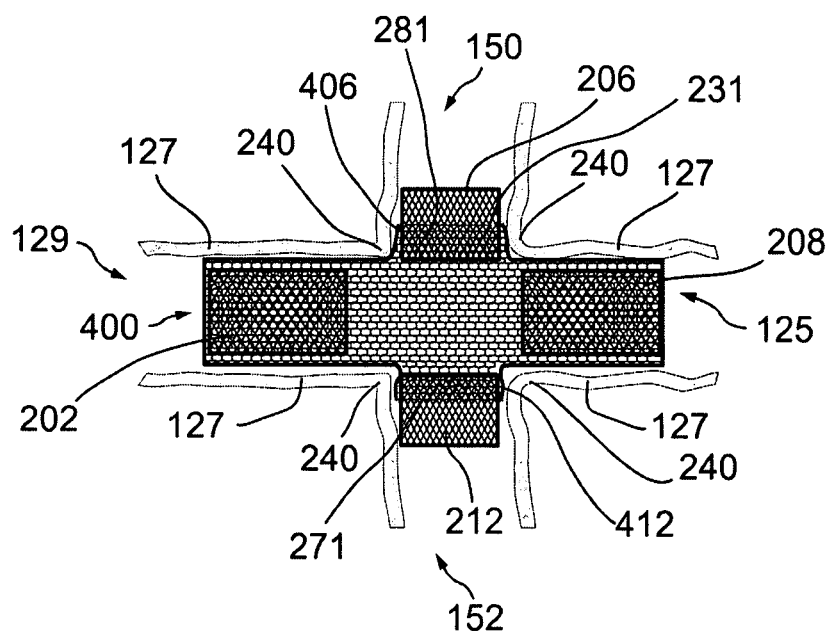

As seen in FIG. 4e, an encircling portion 271 of lower branch sleeve 412, partially covers lower branch stent 212 while an encircling portion 281 of upper branch sleeve 406 partially covers upper branch stent 206, thereby providing support of stenotic tissue 240 therebetween.

Figure 5A:
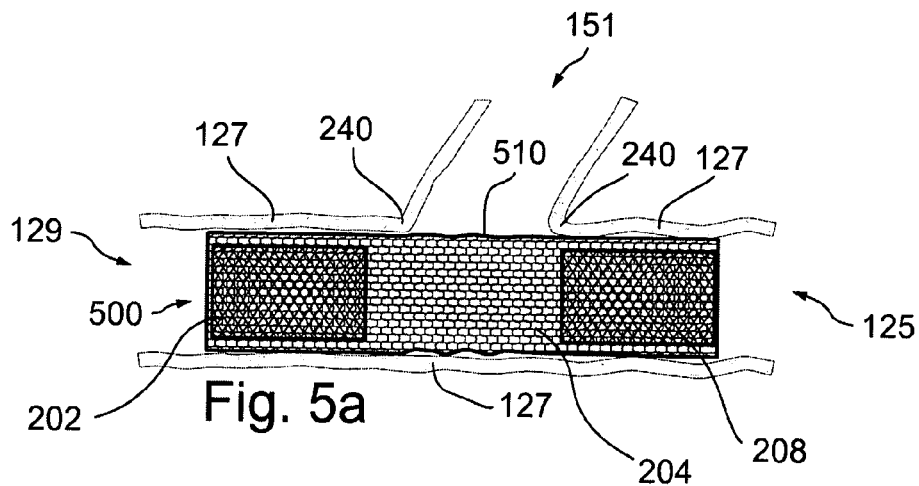
Figure 5B:
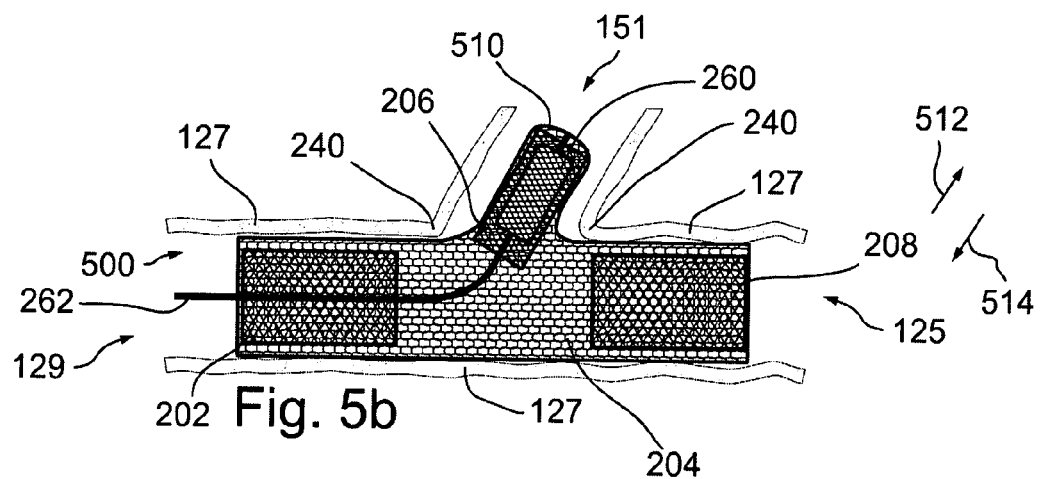

Referring to FIG. 5a, a stent assembly 500 has been positioned and expanded so that proximal stent 202 is positioned in proximal lumen 129 and distal stent 208 is positioned in distal lumen 125. Stent jacket 204, positioned between stents 202 and 208, includes a stretchable material 510. As seen in FIG. 5b, balloon 260, surrounded by unexpanded upper branch stent 206 has been pressed into stretchable material 510, causing stent jacket 204 to bulge into upper branch lumen 151.

Figure 5C:
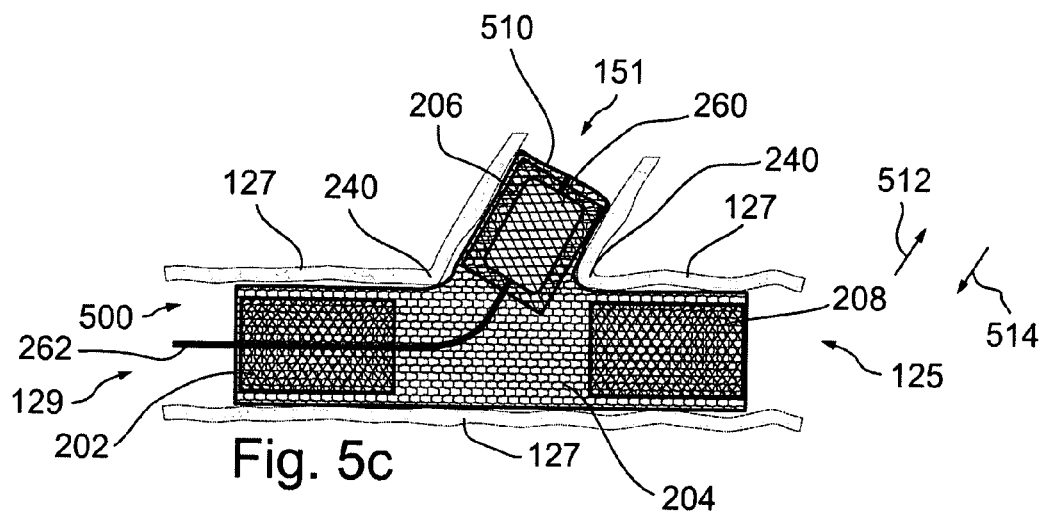

In FIG. 5c, balloon 260 has been expanded, thereby causing a partial expansion of upper branch stent 206. Partially expanded upper branch stent 206 stretches stretchable material 510, creating considerable tension on the portion of stent jacket 204 that spans upper branch lumen 151.

Figure 5D:
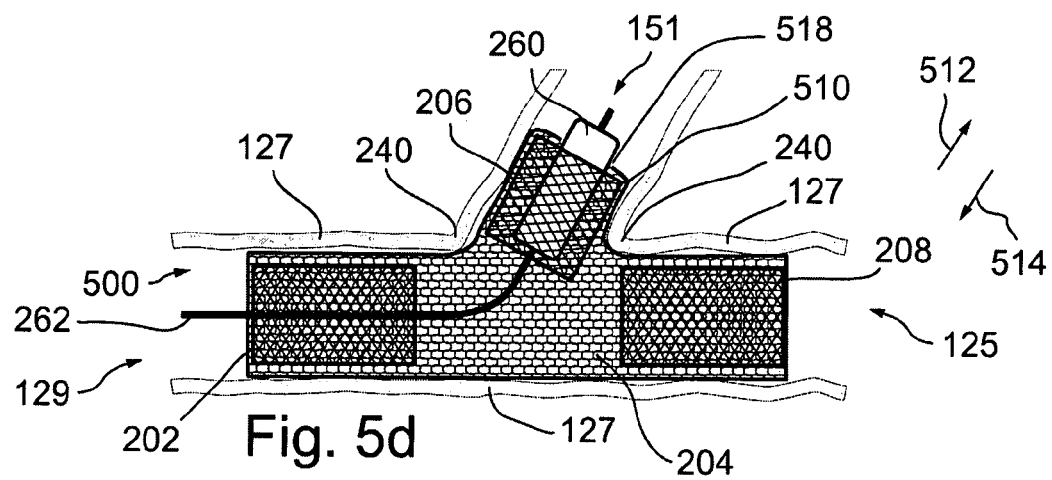

In FIG. 5d, balloon 260 has been partially deflated and pressed in an upward direction 512, thereby puncturing material 510 and creating an opening 518. Partially deflated balloon 260 is then moved in a downward direction 514 and partially inflated to expand and be secured within upper branch stent 206. Balloon 260 and upper branch stent 206 are then moved in upward direction 514 causing upper branch stent 206 to pass through opening 518 and into upper branch lumen 151.

Figure 5E:
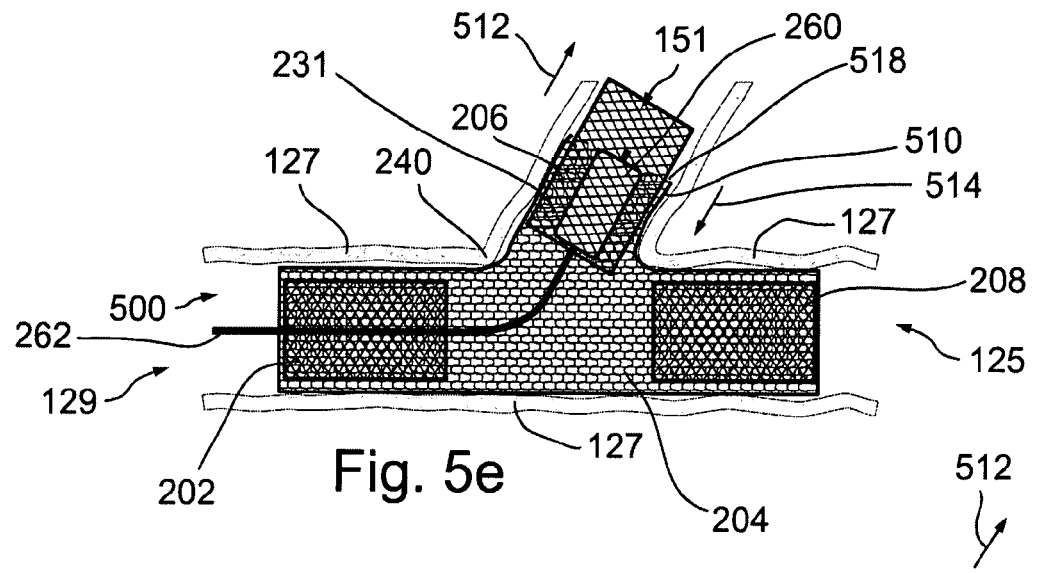

Balloon 260 is then fully expanded to cause upper branch stent 206 to fully expand. As seen in FIG. 5e, upper branch stent 206 is partially covered by stretchable material 510, fully expanded in upper branch lumen 151 while balloon 260 has been deflated and is being moved in direction 514 to be removed percutaneously from artery 127.

Referring to FIG. 6a, a stretch stent assembly 600 has been positioned and expanded so that proximal stent 202 is positioned in proximal lumen 129 and distal stent 208 is positioned in distal lumen 125. As seen in FIG. 6b, balloon 260, has been pressed into stretchable material 510, causing stent jacket 204 to bulge into upper branch lumen 151.

Figure 6D:
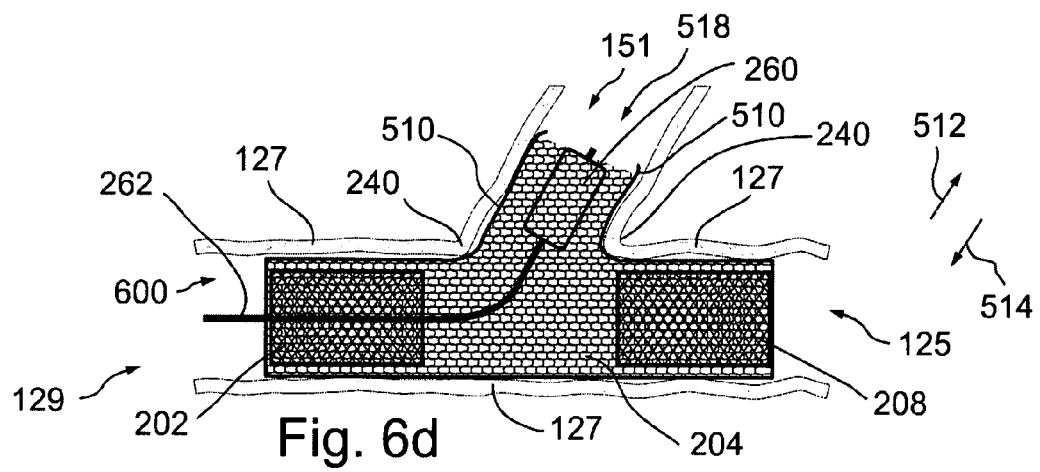
Figure 6E:
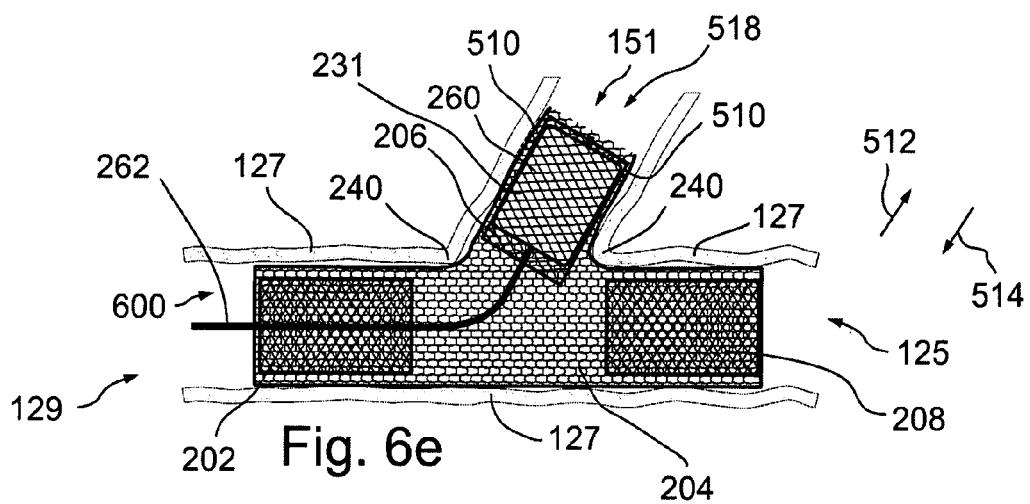

In FIG. 6c, balloon 260 has been fully expanded, thereby puncturing material 510 and creating opening 518. In FIG. 6d, balloon 260 has been partially deflated and pulled downward in direction 514. Following loading of upper branch stent 206, as seen in FIG. 6e, balloon 260 is partially inflated to move upper branch stent 206 through opening 518. With upper branch stent 206 properly positioned in upper lumen 151, balloon 260 is then fully expanded so that upper branch stent 206 expands to fully open upper branch lumen 151.

Figure 6F:
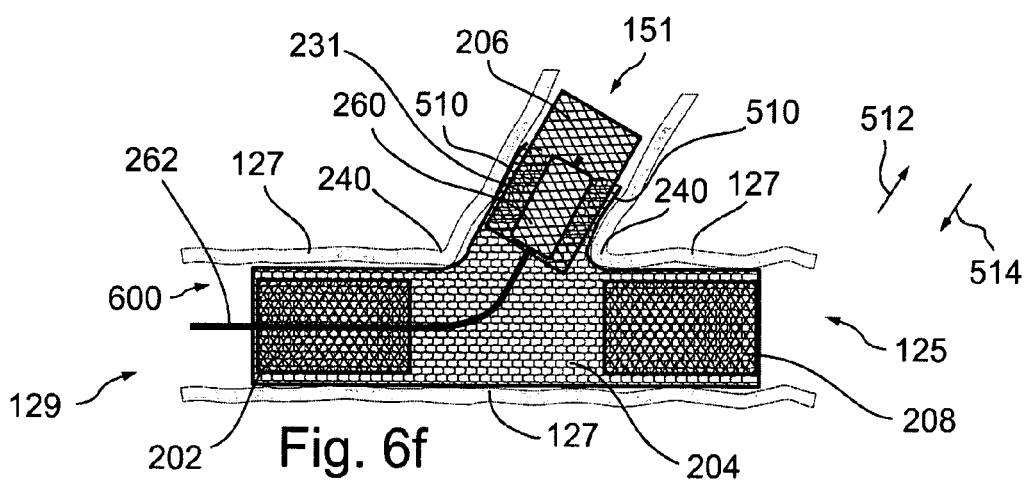

Balloon 260 is then deflated and pulled percutaneously in proximal direction 514 and removed from arteries 127. FIG. 6f shows branch stent 206 fully expanded in branch lumen 151 and balloon 260 being removed in direction 514.

Figure 7A:
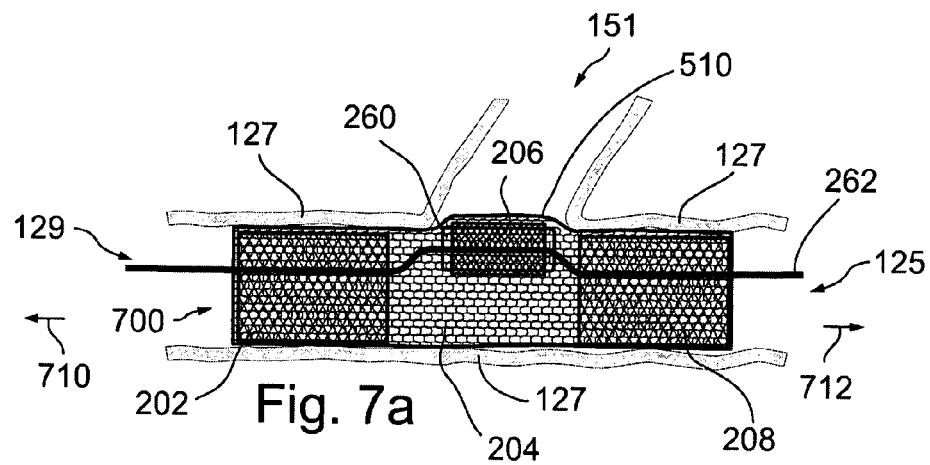

Referring to FIG. 7a, assembly 700 has been positioned and expanded so that proximal stent 202 is positioned in proximal lumen 129 and distal stent 208 is positioned in distal lumen 125. A catheter 262 spans from distal lumen 125 through proximal lumen 129 and is positioned adjacent to upper branch lumen 151 with upper branch stent 206 surrounding balloon 260.

Figure 7B:
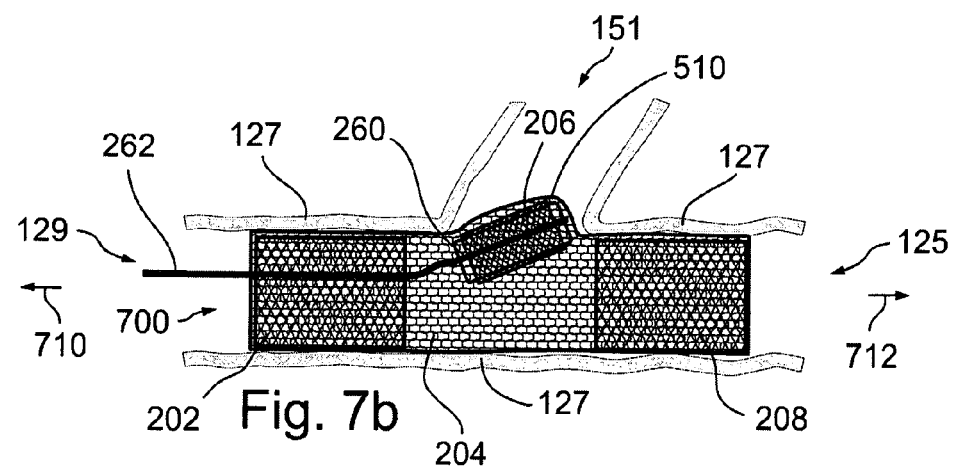

In embodiments, as seen in FIG. 7b, catheter 262 is pulled in a proximal direction 710 until the distal portion of catheter 262 is fully contained within balloon 260. Catheter 262 is then moved in a distal direction 712 to cause stretchable material 510 to bulge into upper branch lumen 151.

Figure 7C:
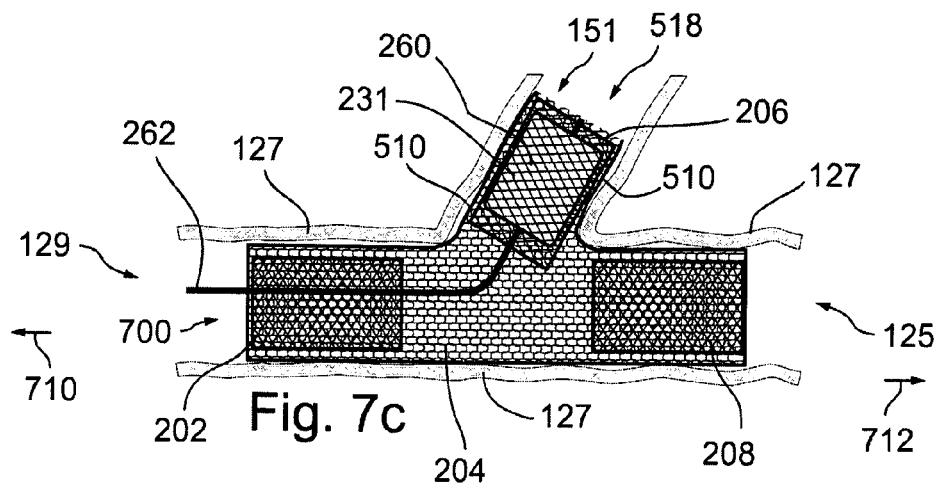
Figure 7D:
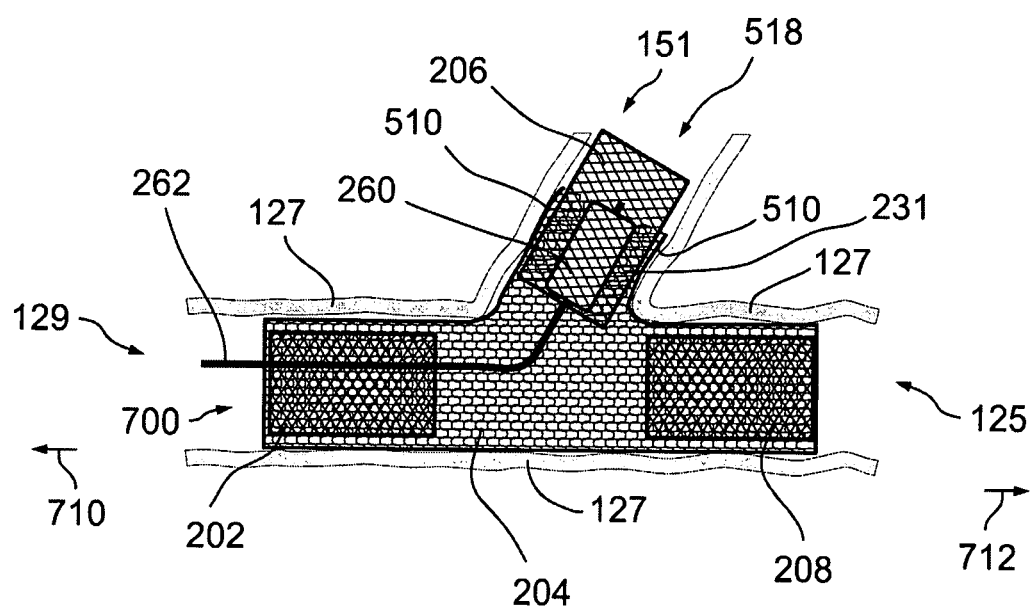

As seen in FIG. 7c, balloon 260 has been expanded, thereby expanding upper branch stent 206, piercing material 510 and creating opening 518. As seen in FIG. 7d, balloon 260 has been deflated, leaving upper branch stent 206 partially covered by stent jacket 204.

Figure 8A:
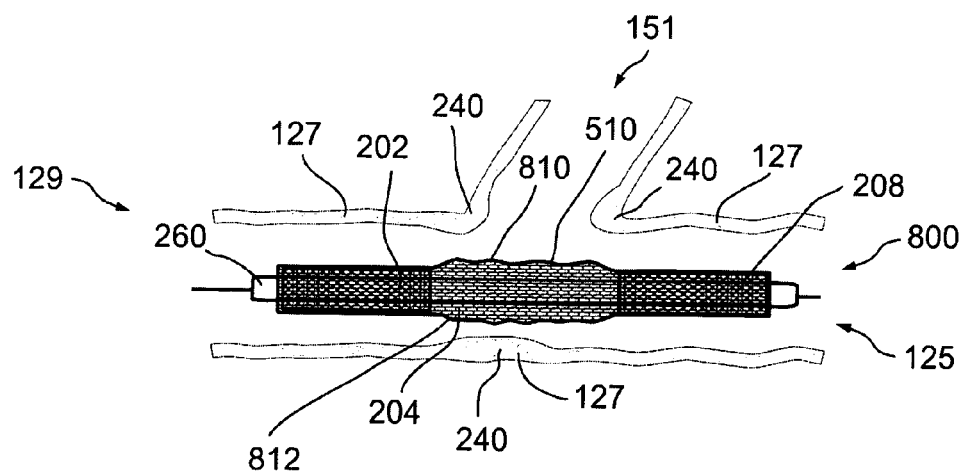
Figure 8B:
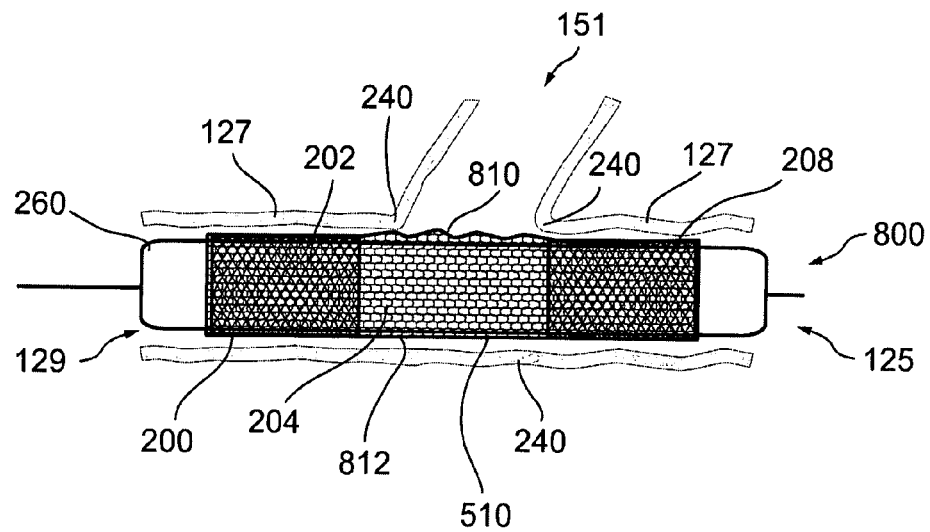

Referring to FIG. 8a, stent system 800 comprises a jacket having billowing walls 812 that include an upper billowing wall potion 810. In embodiments, billing walls include a biocompatible adhesive so that upon inflation, balloon 260 presses billowing wall 812 against artery 127, thereby creating folds in billowing walls 812.

Figure 8C:
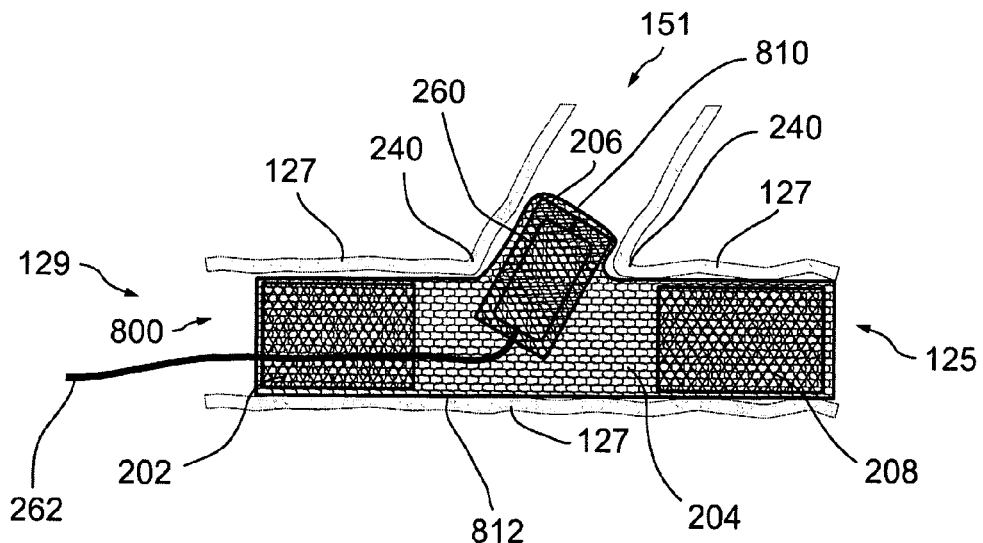

As balloon 260 continues to expand, folds in billowing wall 812 are compressing to adhere to each other and compressed against artery 127. In distinct contrast, as seen in FIG. 8c, upper billowing wall portion 810 is adjacent to upper branch lumen 151, is pressed into branch lumen 151 and does not form adherent folds.

Figure 8D:
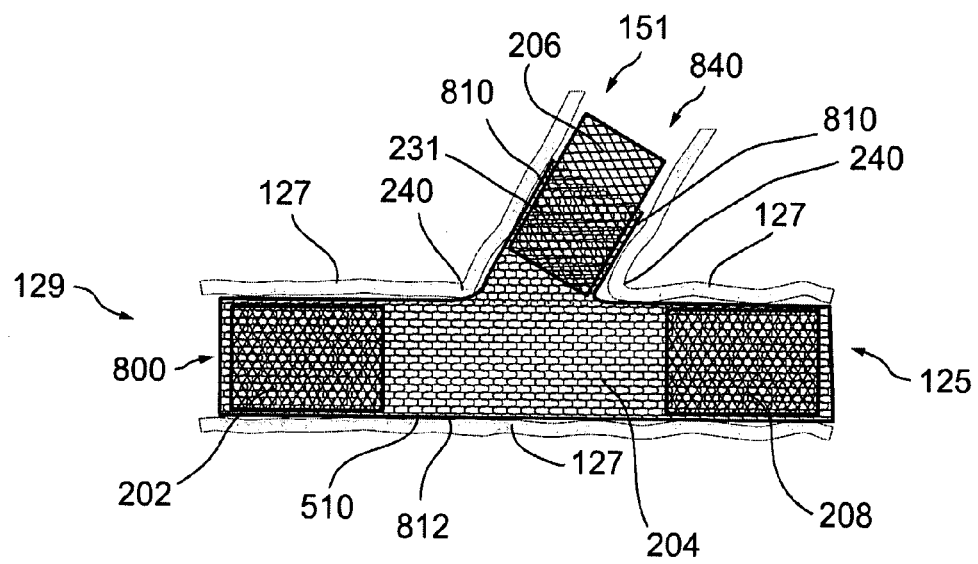

As seen in FIG. 8d further expansion of upper branch stent 206 punctures stent jacket 204, creating a punctured opening 840 and upper branch stent 206 has opened upper branch lumen 151.

As used herein, the terms proximal and proximally refer to a position and a movement in an upstream direction from lumen 129 toward vessel lumen 151. As used herein, the terms distal and distally refer to a position and a movement, respectively, in a downstream direction from lumen 151 toward lumen 129. In embodiments, stent jacket 204 has a thickness of at least about 20 microns and no more than about 200 microns.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A stent system adapted to expand in vivo in a patient's vessel, the stent system comprising:
   a) first and second radially expandable mesh stents adapted to expand from a contracted state to a radially expanded state, wherein said first stem is separated by a predetermined distance from said second stent; and b) a stent jacket comprising a mesh structure formed of a plurality of fibers defining apertures having a center dimension of at least 180 micrometers that are limited by the fibers having a diameter of about 7 micrometers to 18 micrometers, the stent jacket spanning said predetermined distance such that a first end of said jacket is disposed over said first stem and a second end of said jacket is disposed over said second stent; and c) a third stent axially disposed and movably set on a guide wire, wherein said stent racket is configured to encircle the axially disposed third stent in a contracted state, while said stent system is being delivered to an in situ location in the patient's vessel with the first and second stents in the contracted state, wherein said stem jacket comprises at least one aperture in the mesh structure sized and dimensioned to allow passage of the guide wire and third stent, and the guide wire is configured to be manipulated through the aperture while said third stent is contracted, and wherein the third stent is configured to move along the guide wire through the at least one aperture at an angle to an axis running between said first and second stent.

2. The stent system according to claim 1, wherein upon radial expansion of said first and second stems, said first jacket end expands radially and encircles at least a portion of said first stent and said second end of said jacket expands radially and encircles at least a portion of said second stent.

3. The stent system according to claim 1, wherein said stent jacket spanning said distance is configured to encircle the axially disposed third stent in the contracted state following delivery of said first and second stents to an in situ location.

4. The stent system according to claim 1, wherein said at least one aperture is additionally configured to encircle an outer surface of said third stent while said third stent is contracted.

5. The stent system according to claim 4, wherein the angle is at least about 15 degrees and no more than about 165 degrees.

6. The stent system according to claim 4, wherein the mean diameter of said at least one aperture is configured to expand when said contracted third stent is expanded while encircled by said aperture.

7. The stent system according to claim 6, wherein upon expansion of said third stent, at least a portion of said stent jacket spanning said distance is configured to encircle at least a portion of an outer surface of said third stent.

8. The stent system according to claim 7, wherein during expansion, said first stent and said second stent are of a sufficient diameter to press at least a portion of the inner walls of a parent vessel with a pressure of at least one atmosphere and no more than about 50 atmospheres.

9. The stent system according to claim 7, wherein during expansion, said first stent and said second stem are of a sufficient diameter to press at least a portion of the inner walls of a parent vessel with a pressure of about 15 atmospheres.

10. The stent system according to claim 7, wherein during expansion, said third stent is of a sufficient diameter to press at least a portion of the inner walls of a branch vessel with a pressure of at least one atmosphere and no more than about 50 atmospheres.

11. The stent system according to claim 10, wherein during expansion, said third stent is of a sufficient diameter to press at least a portion of the inner walls of a branch vessel with a pressure of about 15 atmospheres.

12. The stent system according to claim 7, wherein during expansion, said first stent and said third stent are of a sufficient diameter to press at least a portion of the inner walls of a parent vessel with a pressure of at least one atmosphere and no more than about 50 atmospheres.

13. The stent system according to claim 12, wherein during expansion, said first stent and said third stent are of a sufficient diameter to press at least a portion of the inner walls of a parent vessel with a pressure of about 15 atmospheres.

14. The stent system according to claim 7, wherein during expansion, said second stent is of a sufficient diameter to press at least a portion of the inner walls of a branch vessel with a pressure of at least one atmosphere and no more than about 50 atmospheres.

15. The stent system according to claim 14, wherein during expansion, said second stent is of a sufficient diameter to press at least a portion of the inner walls of a branch vessel with a pressure of about 15 atmospheres.

16. The stent system according to claim 1, wherein said third stent, following expansion of said first stent and said second stent, is configured to have an end pressed into a portion of said stent jacket.

17. The stent system according to claim 16, wherein said pressed portion of said stent jacket is configured to stretch when said third stent is expanded during said pressing.

18. The stent system according to claim 17, wherein said stretched portion of said stent jacket is configured to be punctured by a puncturing tool, wherein the resulting puncture is of a sufficient diameter to allow said third stent to pass through said puncture.

19. The stent system according to claim 18, wherein said third stent is configured to pass through said puncture at an angle to an axis running between said first and second stent, said angle being at least about 15 degrees and no more than about 165 degrees.

20. The stent system according to claim 19, wherein a portion of said stent jacket spanning said distance remains substantially intact following said puncturing.

21. The stent system according to claim 18, wherein said puncturing tool comprises an expandable balloon.

22. The stent system according to claim 21, wherein said stent jacket spanning said distance comprises at least one aperture configured to encircle said expandable balloon in a contracted state.

23. The stent system according to claim 22, wherein said at least one aperture is configured to rip as said expandable balloon is inflated.

24. The stent system according to claim 18, wherein upon passage of said third stent through said puncture, at least a portion of said jacket is configured to encircle at least a portion of an outer surface of said third stent.

25. The stent system according to claim 24, wherein during expansion, said first stent and said second stent are of a sufficient diameter to press at least a portion of the inner walls of a parent vessel with a pressure of at least one atmosphere and no more than about 50 atmospheres.

26. The stent system according to claim 25, wherein during expansion, said first stent and said second stent are of a sufficient diameter to press at least a portion of the inner walls of a parent vessel with a pressure of about 15 atmospheres.

27. The stent system according to claim 24, wherein during expansion, said third stent is of a sufficient diameter to press at least a portion of the inner walls of a branch vessel with a pressure of at least one atmosphere and no more than about 50 atmospheres.

28. The stent system according to claim 27, wherein during expansion, said third stent is of a sufficient diameter to press at least a portion of the inner walls of a branch vessel with a pressure of about 15 atmospheres.

29. The stent system according to claim 27, wherein during expansion said stents are configured to expand in a manner that dilates the adjacent vessels.

30. The stent system according to claim 27, wherein following expansion the vessels are supported with one layer of stent metal.

31. The stent system according to claim 24, wherein during expansion, said first stem and said third stent are of a sufficient diameter to press at least a portion of the inner walls of a parent vessel with a pressure of at least one atmosphere and no inure than about 50 atmospheres.

32. The stent system according to claim 31, wherein during expansion, said first stent and said third stent are of a sufficient diameter to press at least a portion of the inner walls of a parent vessel with a pressure of about 15 atmospheres.

33. The stent system according to claim 24, wherein during expansion, said second is of a sufficient diameter to press at least a portion of the inner walls of a branch vessel with a pressure of at least one atmosphere and no more than about 50 atmospheres.

34. The stent system according to claim 33, wherein during expansion, said second stent is of a sufficient diameter to press at least a portion of the inner wails of a branch vessel with a pressure of about 15 atmospheres.

35. The stent system according to claim 1, wherein said stents comprise a metallic base from the group consisting of stainless steel, nitinol, tantalum, MP35N alloy, a cobalt-based alloy, a cobalt-chromium alloy, platinum, titanium, and other biocompatible metal alloy.

36. The stent system according to claim 1, wherein said stents are selected from the group consisting of a cardiovascular stent, a peripheral stent, a coronary stent, an abdominal aortic aneurysm stent, a cerebral stent, a carotid stem, an endovascular stent, an aortic valve stent, and a pulmonary valve stent.

37. The stent system according to claim 1, wherein said stent jacket comprises a material manufactured by a process from the group consisting of interlacing knitting, interlocked knitting, braiding, interlacing, and dipping a porous mold into one or more reagents.

38. The stent system of claim 1, wherein one or more of the first, second, and third stents and the stent jacket is coated or imbued with one or more active pharmaceutical agents.

39. The stent system of claim 38, wherein the one or more active pharmaceutical agents comprises a chemotherapeutic, an analgesic, an antihistamine, a corticosteroid, a hormone, a non-steroidal anti-inflammatory agent, or a vasodilator.

* * * * *

UNITED STATES PATENT AND TRADEMARK OFFICE
CERTIFICATE OF CORRECTION

PATENT NO.         : 8,961,586 B2
APPLICATION NO.    : 11/797168
DATED              : February 24, 2015
INVENTOR(S)        : Holzer et al.

Page 1 of 1

It is certified that error appears in the above-identified patent and that said Letters Patent is hereby corrected as shown below:

In the Claims

Claim 1 Column 15, line 1: change --stem-- to "stent".

Claim 1 Column 15, line 9: change --stem-- to "stent".

Claim 1 Column 15, line 12: change --racket-- to "jacket".

Claim 1 Column 15, line 17: change --stem-- to "stent".

Claim 2 Column 15, line 26: change --stems-- to "stents".

Claim 31 Column 17, line 10: change --stem-- to "stent".

Claim 31 Column 17, line 13: change --inure-- to "more".

Claim 34 Column 17, line 25: change --wails-- to "walls".

Claim 36 Column 18, line 9: change --stem-- to "stent".

Signed and Sealed this
Twenty-fifth Day of August, 2015

Michelle K. Lee
*Director of the United States Patent and Trademark Office*